(12) United States Patent
Baum et al.

(10) Patent No.: US 10,451,540 B2
(45) Date of Patent: Oct. 22, 2019

(54) MULTI-PASS GAS CELL WITH MIRRORS IN OPENINGS OF CYLINDRICAL WALL FOR IR AND UV MONITORING

(71) Applicant: ENTEGRIS, INC., Billerica, MA (US)

(72) Inventors: Thomas H. Baum, New Fairfield, CT (US); John P. Coates, Newtown, CT (US); Robert L. Wright, Jr., Newtown, CT (US)

(73) Assignee: ENTEGRIS, INC., Billerica, MA (US)

( * ) Notice: Subject to any disclaimer, the term of this patent is extended or adjusted under 35 U.S.C. 154(b) by 72 days.

(21) Appl. No.: 15/544,327

(22) PCT Filed: Jan. 16, 2016

(86) PCT No.: PCT/US2016/013751
§ 371 (c)(1),
(2) Date: Jul. 18, 2017

(87) PCT Pub. No.: WO2016/118431
PCT Pub. Date: Jul. 28, 2016

(65) Prior Publication Data
US 2018/0011003 A1 Jan. 11, 2018

Related U.S. Application Data

(60) Provisional application No. 62/105,178, filed on Jan. 19, 2015.

(51) Int. Cl.
*G01N 21/03* (2006.01)
*G01N 21/31* (2006.01)

(52) U.S. Cl.
CPC ........... *G01N 21/031* (2013.01); *G01N 21/31* (2013.01); *G01N 2201/0636* (2013.01)

(58) Field of Classification Search
CPC ................. G01N 21/031; G01N 21/31; G01N 2201/0636
See application file for complete search history.

(56) References Cited

U.S. PATENT DOCUMENTS 3,815,977 A * 6/1974 Vasiliev .................... G01J 1/04
359/834
4,322,621 A * 3/1982 Aagard ................ G01N 21/031
250/343

(Continued)

FOREIGN PATENT DOCUMENTS

CN 101109701 A 1/2008
CN 101400989 A 4/2009

(Continued)

OTHER PUBLICATIONS

Mid-infrared spectroscopy for gases and liquids based on quantum cascade technologies,Analyst, The Royal Society of Chemistry, Mar. 23, 2013, doi: 10.1039/c3an01462b.

(Continued)

*Primary Examiner* — Hwa Andrew Lee
(74) *Attorney, Agent, or Firm* — ENTEGRIS, INC.

(57) ABSTRACT

A multipass cell assembly for monitoring of fluid is described, as well as fluid processing systems utilizing same, and associated methods of use of such multipass cell assembly for fluid monitoring. The multipass cell assembly is usefully employed in fluid processing operations such as monitoring of vapor deposition process reactants, e.g., reactants used for vapor deposition metallization of tungsten from a tungsten carbonyl precursor.

15 Claims, 24 Drawing Sheets

(56) References Cited

U.S. PATENT DOCUMENTS

| | | | |
|---|---|---|---|
| 5,220,402 A * | 6/1993 | Harvey | G01N 21/031 356/246 |
| 5,726,752 A * | 3/1998 | Uno | G01N 21/031 356/244 |
| 5,818,578 A | 10/1998 | Inman | |
| 6,940,600 B1 * | 9/2005 | Smith | G01N 21/031 356/437 |
| 7,449,694 B2 | 11/2008 | Yi et al. | |
| 7,911,671 B2 * | 3/2011 | Rabb | G02B 17/004 359/201.2 |
| 7,936,460 B2 | 5/2011 | Iwase et al. | |
| 9,052,232 B2 * | 6/2015 | Smith | G01J 3/0291 |
| 9,638,624 B2 * | 5/2017 | Mangold | G01N 21/3504 |
| 10,067,049 B1 * | 9/2018 | Bambha | G01N 15/1434 |
| 2002/0185603 A1 | 12/2002 | Daly et al. | |
| 2004/0015300 A1 | 1/2004 | Ganguli et al. | |
| 2006/0068097 A1 | 3/2006 | Yamasaki et al. | |
| 2006/0227327 A1 * | 10/2006 | McNeal | G01N 21/031 356/436 |
| 2008/0252892 A1 * | 10/2008 | Pralle | G01N 21/0303 356/440 |
| 2009/0039284 A1 * | 2/2009 | Goto | G01J 3/02 250/432 R |
| 2010/0079760 A1 * | 4/2010 | Bernacki | G01N 21/031 356/437 |
| 2012/0261578 A1 | 10/2012 | Scott et al. | |
| 2014/0036347 A1 * | 2/2014 | Tedesco | G01J 3/44 359/334 |
| 2018/0011003 A1 * | 1/2018 | Baum | G01N 21/031 |

FOREIGN PATENT DOCUMENTS

| | | |
|---|---|---|
| CN | 101872062 A | 10/2010 |
| JP | H04-274737 A | 9/1992 |
| JP | H08-043305 A | 2/1996 |
| JP | H09-222392 A1 | 8/1997 |
| JP | H11-513805 A1 | 11/1999 |
| JP | 2000-206035 A1 | 7/2000 |
| JP | 2003-014637 A1 | 1/2003 |
| JP | 2004-069381 A1 | 3/2004 |
| JP | 2005-147962 A1 | 6/2005 |
| JP | 2006-153815 A1 | 6/2006 |
| JP | 2007-514160 A1 | 5/2007 |
| JP | 2008-515234 A1 | 5/2008 |
| JP | 2011-035366 A1 | 2/2011 |
| KR | 10-2007-0000436 A1 | 1/2007 |
| KR | 10-2009-0086766 A1 | 8/2009 |
| WO | 9715817 A1 | 5/1997 |
| WO | 2016/118431 A1 | 7/2016 |

OTHER PUBLICATIONS

Tuzson, Bela, et al., "Compact multipass optical cell for laser spectroscopy Mid-infrared spectroscopy", Optics Letters, vol. 38, No. 3, pp. 257-259(Feb. 1, 2013).

* cited by examiner

MULTI-PASS GAS CELL WITH MIRRORS IN OPENINGS OF CYLINDRICAL WALL FOR IR AND UV MONITORING

CROSS-REFERENCE TO RELATED APPLICATION

This application claims the benefit of priority under the provisions of 35 U.S.C. § 119 of U.S. Provisional Patent Application No. 62/105,178 filed Jan. 19, 2015 in the names of Thomas H. Baum, et al. for "SMALL VOLUME, LONG PATHLENGTH MULTI-PASS GAS CELL FOR IR AND UV MONITORING". The disclosure of such U.S. Provisional Patent Application No. 62/105,178 is hereby incorporated herein in its entirety, for all purposes.

FIELD

The present disclosure relates to a fluid monitoring apparatus and method that enables small-volume, long path length optoelectronic monitoring of fluids in applications such as manufacturing of semiconductor products, flat-panel displays, and solar panels. Optical cells are described, which provide for increased sensitivity of measurement of fluidic materials such as liquids and gases within a constrained volume. Such optical cells employ multiple reflections from walls of an optical cavity, and are particularly usefully employed for measurement and detection of low concentrations of gases or vapors, in a wide range of applications, e.g., industrial, environmental, public safety, homeland defense, consumer, and medical applications.

DESCRIPTION OF THE RELATED ART

In the use of optoelectronic detectors for monitoring of fluids, e.g., to quantitate or characterize components of interest in fluid streams, infrared monitoring devices have been developed. These devices may be of widely varied type.

In one category of such devices, infrared radiation is passed through a sample cell to interact with a fluid stream flow through the cell. The infrared radiation source utilized in such devices is typically a broadband infrared light source that is configured to produce a collimated beam. The beam contacts the fluid stream, which typically is gas, but may comprise a liquid or gas/liquid mixture. In such contact, the beam of incident radiation interacts with components of the stream and a transmitted or reflected signal passes out of the sample cell and impinges on an infrared detector.

The infrared detector may be variously configured. For example, it may comprise multiple independent filter channels, each equipped with a specific filter element that permits passage of infrared radiation of a particular spectral character. The independent filter elements thus may be employed to identify specific components or chemical species of interest, which interact with the infrared light from the IR light source and produce a distinctive alteration, attenuation, or modulation of such infrared light, so that the infrared light output from the sample cell is identifiable as being associated with such components or chemical species.

The infrared detector may for example comprise IR filters that are arranged with receiving thermopile (pyroelectric, etc.) elements that convert the infrared heat energy into electrical energy, e.g., a DC output signal. The thermopile element associated with a specific filter may therefore be "tuned" to responsively generate an output electrical signal when the thermopile element is impinged with IR radiation of a specific wavelength or other spectral character that is determined by the associated filter.

The aforementioned infrared fluid monitoring devices can be applied to numerous materials and applications. Broadly, the fluid monitoring devices of the present disclosure may be embodied in any of variant configurations and forms, and may for example encompass pyroelectric detectors of widely varying type.

As a specific example, a thermopile infrared (TPIR) monitoring system may be employed in a semiconductor manufacturing facility in which metallization, e.g., tungsten metallization is being carried out by a vapor deposition process using a corresponding metal precursor, with the TPIR monitoring system being configured to monitor the effluent stream from the vapor deposition process to detect effluent concentrations of the precursor and its vapor decomposition products generated in the process. The detector utilized in such TPIR monitoring system may include a reference channel that is utilized for baseline reference or calibration purposes.

The above-described optoelectronic monitoring systems in use must address competing design considerations. In general, the path of the infrared beam passing through the fluid stream in the sample cell is desirably of substantial length to enable corresponding interaction of the incident IR beam with the fluid stream to achieve a high level of accuracy (and resolution) in the detection operation. Thus, long path lengths allow low detection limits to be realized. At the same time, particularly in applications such as the semiconductor industry in which space is expensive and desirably minimized, it is desirable to provide the monitoring system with a compact character so that it correspondingly has a small volume and small form factor or footprint.

In addition to infrared light source optoelectronic monitoring systems for detection and analysis of components of multicomponent fluid streams, optoelectronic monitoring systems utilizing other types of light sources, including visible light sources, ultraviolet (UV) light sources, etc., are utilized in the art.

Fluid monitoring systems of the above-described types require an optical path length of appropriate size for interaction of the specific electromagnetic radiation, e.g., light, with the material being monitored, and as mentioned above, the path length determines the sensitivity and lower detection limits of the measurement that is achievable by a specific monitoring device. The absorption of the electromagnetic radiation is proportional to the path length, in accordance with Lambert's Law, or more universally by the Beer-Lambert-Bouguer Law. Path length considerations can limit practical use of monitoring apparatus in many applications in which low concentrations of gases or vapors need to be measured. It is not uncommon that path lengths of 1 meter or greater are needed for measurement of materials in concentration ranges of low parts per million down to parts per billion or lower.

In order to achieve a long path-length in the sample cell while concurrently achieving a small size, small volume configuration, multi-pass monitoring systems have been proposed and developed. Such small-volume, long path length fluid sample cells employ multiple passes or reflections of the incident radiation beam to achieve the long path-length in a relatively small form factor. Small volumes enable time delays to be reduced while long path lengths enable lower detection limits.

Thus, primary considerations in the achievement of useful optoelectronic fluid monitoring cells are the achievement of low sample volume requirements for the monitoring operation, extended path length for optical monitoring to realize improved sample measurement sensitivity, efficient optical coupling of components to maximize optical signal utilization, and low-cost manufacturability of the fluid monitoring cell and associated parts and assemblies.

The art continues to seek improvements in optoelectronic monitoring systems for detection and analysis of components of multicomponent fluid streams, and for real-time fluid stream monitoring.

SUMMARY

The present disclosure relates to fluid monitoring apparatus and methods.

In one aspect, the disclosure relates to a multipass cell assembly for monitoring of fluid, comprising:

an arcuate circumscribing member defining a multipass optical reflection chamber, the arcuate circumscribing member comprising inwardly facing reflective surface along an arcuate extent thereof that generates multipass optical reflection of light impinged thereon;

a light input structure configured to direct light from a light source onto the reflective surface of the arcuate circumscribing member so that said multipass optical reflection of light is generated in the optical reflection chamber;

a light output structure configured to direct multipassed light from the reflective surface of the arcuate circumscribing member out of the optical reflection chamber for detection and processing thereof;

a fluid inlet configured to introduce fluid to the multipass optical reflection chamber so that it interacts with multipassing light therein; and a fluid outlet configured to discharge fluid from the multipass optical reflection chamber after interaction with multipassing light therein.

In another aspect, the disclosure relates to a multipass cell assembly for monitoring of fluid, comprising:

a cylindrical wall member circumscribing and defining a multipass optical reflection chamber, the cylindrical wall member comprising circumferentially spaced-apart openings therein;

mirrors in the circumferentially spaced apart openings, the mirrors being inwardly facing and configured to generate multipass optical reflection of light in the multipass optical reflection chamber;

a light input structure configured to direct light from a light source onto a reflective surface of one or more of the mirrors so that said multipass optical reflection of light is generated in the optical reflection chamber;

a light output structure configured to direct multipassed light out of the optical reflection chamber for detection and processing thereof;

floor and cover members that cooperatively engage with the cylindrical wall member to enclose the multipass optical reflection chamber;

a fluid inlet configured to introduce fluid to the multipass optical reflection chamber so that it interacts with multipassing light therein, said fluid inlet comprising at least one fluid inlet port in the floor member;

a fluid outlet configured to discharge fluid from the multipass optical reflection chamber after interaction with multipassing light therein, said fluid outlet comprising at least one fluid outlet port in the floor member;

a light source mounted on the cover member and optically coupled to the light input structure; and a light detector mounted on the cover member and optically coupled light output structure.

In a further aspect, the disclosure relates to a fluid processing system, comprising:

a process tool utilizing or generating a fluid stream; and a multipass cell assembly for monitoring of fluid, as variously described herein, configured for flow of the fluid stream through the multipass optical reflection chamber from the fluid inlet to the fluid outlet for interaction with multipassing light in the multipass optical reflection chamber.

A further aspect of the disclosure relates to a method of monitoring a fluid stream, comprising flowing the fluid stream through a multipass cell assembly of the disclosure, as variously described herein, to generate a multipassed light output, and processing the multipassed light output to characterize or analyze the fluid stream.

Other aspects, features and embodiments of the disclosure will be more fully apparent from the ensuing description and appended claims.

DETAILED DESCRIPTION

Figure 1:
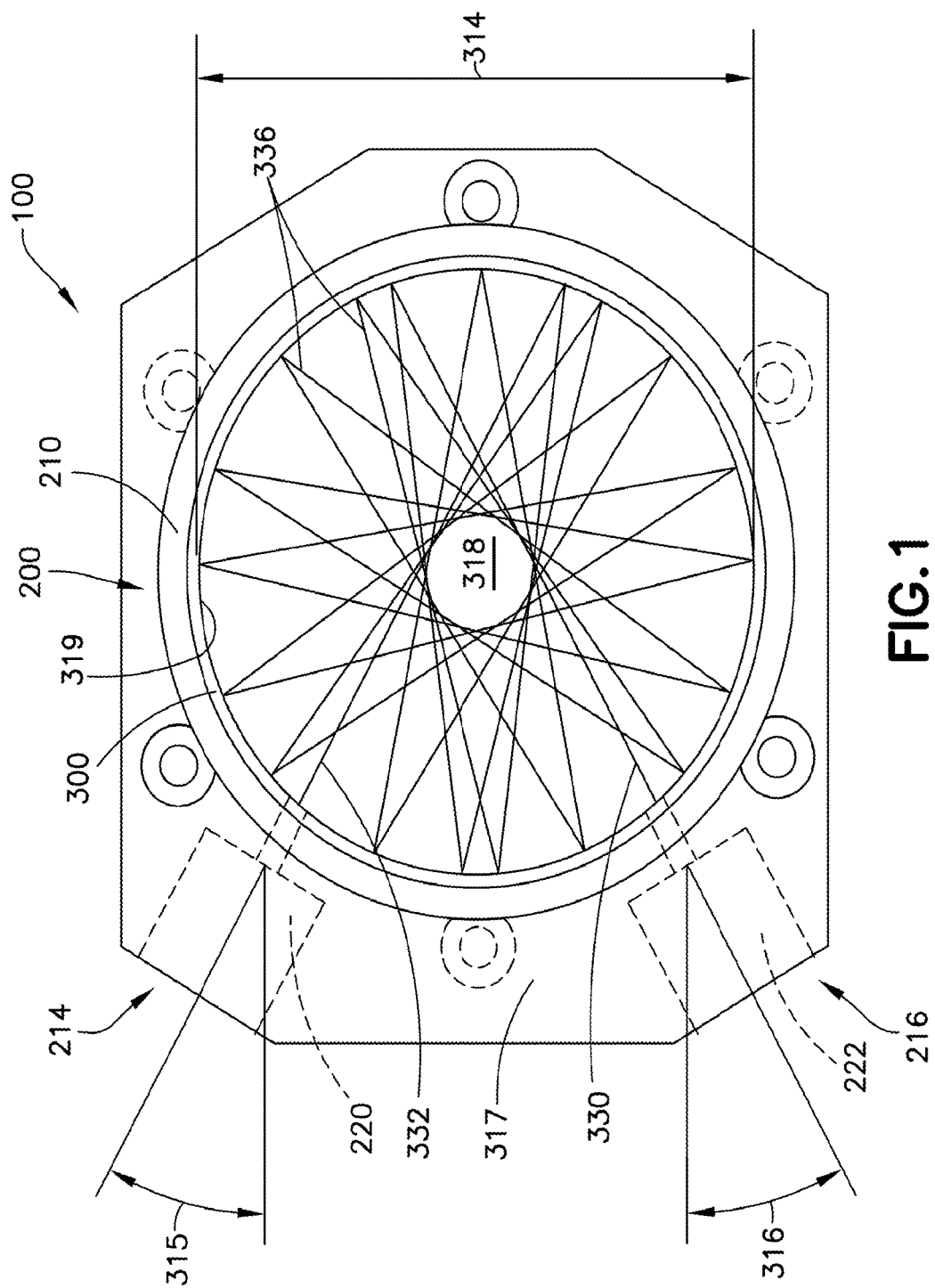
FIG. 1 is a simplified schematic top plan view of a multipass cell assembly of the present disclosure, in one embodiment thereof.

The present disclosure relates to fluid monitoring apparatus and methods, in which a multipass cell assembly of a highly efficient and compact configuration is employed to achieve extended path optical monitoring of fluid.

In one aspect, the disclosure relates to a multipass cell assembly for monitoring of fluid, comprising:

an arcuate circumscribing member defining a multipass optical reflection chamber, the arcuate circumscribing member comprising inwardly facing reflective surface along an arcuate extent thereof that generates multipass optical reflection of light impinged thereon;

a light input structure configured to direct light from a light source onto the reflective surface of the arcuate circumscribing member so that said multipass optical reflection of light is generated in the optical reflection chamber;

a light output structure configured to direct multipassed light from the reflective surface of the arcuate circumscribing member out of the optical reflection chamber for detection and processing thereof;

a fluid inlet configured to introduce fluid to the multipass optical reflection chamber so that it interacts with multipassing light therein; and a fluid outlet configured to discharge fluid from the multipass optical reflection chamber after interaction with multipassing light therein.

In specific arrangements of such multipass cell assembly, the reflective surface may comprise a plurality of mirrors along the arcuate extent of the arcuate circumscribing member. In these arrangements, the arcuate circumscribing member may comprise an arcuate circumscribing support comprising receiving openings therein, in which respective ones of the plurality of mirrors are mounted. The mirrors may comprise parabolic mirrors, or may be of other shape or conformation.

The arcuate circumscribing member in specific embodiments may comprise a cylindrical wall member, e.g., wherein the cylindrical wall member comprises a reflective inner wall surface comprising the inwardly facing reflective surface. Alternatively, the arcuate circumscribing member may comprise a faceted or segmented inner surface comprising the inwardly facing reflective surface.

In various embodiments, the multipass cell assembly may further comprise cover and floor members that cooperatively couple with the arcuate circumscribing member to enclose the multipass optical reflection chamber.

These cover and floor members may comprise interior light-reflective surfaces, so that the cell itself functions in the manner of a light pipe to maximize optical reflection efficiency.

In specific arrangements, the fluid inlet of the multipass cell assembly may include at least one fluid inlet port in the floor member, and the cell assembly in specific embodiments may include two or more such fluid inlet ports, to achieve uniformity in the fluid stream being flowed through the subassembly.

In like manner, the fluid outlet may include at least one fluid outlet port in the floor member, and when the floor member contains fluid inlet ports, the fluid outlet ports may be transversely spaced apart from the fluid inlet, to prevent fluid short-circuiting or other non-uniform or anomalous behavior in the cell assembly.

The light input structure in the multipass cell assembly may comprise a light inlet port, configured to accommodate positioning therein of a light source or alternatively as configured to be optically coupled to a light source, for introduction of incident light into the multipass optical reflection chamber of the cell assembly.

The light output structure in the multipass cell assembly may in like manner comprise a light outlet port, configured to accommodate positioning therein of an output light detector or alternatively as configured to be optically coupled to an output light detector.

In the multipass cell assembly, the relative positions of the light input port and the light output port in relation to one another are desirably arranged to achieve a specific degree of multipassing of the light introduced to the optical reflection chamber, so that the light input and light output of the optical reflection chamber achieve a requisite path length for the specific application in which the multipass cell assembly is employed. The relative positions of the respective light input and light output ports in relation to each other may be widely varied within the broad practice of the present disclosure.

In some embodiments, it may be desired to position the light input port and light output port in relation to one another, to define an included angle therebetween in a range of from 30° to 90°. In other embodiments, it may be desired to position the light input port light output port in relation to one another, to define an included angle therebetween in a range of from 35° to 75°. It will be recognized that optimal positioning of the input and output ports may be readily determined within the skill of the art, based on the disclosure herein, to provide a suitable arrangement for specific implementations of the multipass cell assembly.

The multipass cell assembly may be fabricated of any suitable materials of construction, and may for example comprise metal, ceramic, alloy, polymeric, or composite materials, depending on the specific character and composition of the fluid stream being flowed through the optical reflection chamber of the multipass cell assembly, since it is desired that the materials of construction of the multipass cell assembly be non-reactive with respect to the fluid stream. In some applications, it may be desirable to fabricate the multipass cell assembly, or subassemblies thereof, from materials having high heat capacity, in order to promote isothermality in the operation of the cell assembly. The choice of specific materials of construction may be based on the thermal, physical, chemical, and/or optical character of the materials, to achieve desired performance behavior of the multipass cell assembly. In various embodiments, the arcuate circumscribing member is fabricated from an aluminum composite material, to facilitate isothermal operation of the cell assembly in use.

In a specific embodiment, the arcuate circumscribing member of the multipass cell assembly may comprise a molded or a micro-machined member or a 3-D printed member, to facilitate economic manufacture of the cell assembly. More generally, any suitable methods of manufacture may be employed.

The mirrors that reflective surface components of the multipass cell assembly of the present disclosure may be of any suitable type appropriate to the function and operation of such assembly in specific gas monitoring applications. In some embodiments, the reflective surface of the multipass cell assembly comprises a plurality of mirrors along the arcuate extent of the arcuate circumscribing member, in which each mirror comprises a quartz mirror substrate on which a gold coating reflective surface is deposited, e.g., by vapor deposition technique.

The light input structure of the multipass cell assembly may comprise a light input port in the arcuate circumscribing member of the assembly, and a light source may be disposed in or optically coupled to such light input port. The light source may be of any suitable character, and may in specific implementations comprise an infrared light source, a UV light source, a visible light source, or other light source of specific desired spectral character. The light source preferably provides collimated light to the optical reflection chamber.

The light output structure likewise may comprise a light output port and the arcuate circumscribing member, and a light detector may be disposed in or optically coupled to the light output port.

In various specific embodiments, the multipass subassembly may further comprise cover and floor members cooperatively engaging the arcuate circumscribing number to enclose the multipass optical reflection chamber. The floor member may be integrally formed with the arcuate circumscribing member, or alternatively the floor member may be formed initially as a separate member that is secured to the arcuate circumscribing member, e.g., by raising, welding, adhesive bonding, mechanical fastening, or other suitable technique. The cover member may likewise be cooperatively engaged with the arcuate circumscribing member in any suitable manner, and may take the form of a detachable cover that is mechanically fastened to the arcuate circumscribing member.

In a particular arrangement, the cell assembly including the cover and floor members may further include a light source mounted on the cover member and optically coupled to the light input structure, and a light detector mounted on the cover member and optically coupled to the light output structure. Such arrangement permits ready access to the light source and light detector subassemblies for servicing, replacement, etc.

The light source in a specific implementation may comprise an infrared light source, and the corresponding light detector may comprise an infrared light detector, e.g., a multi-channel infrared light detector. (The source could be broadband or a specific band of energy). Such infrared light detector may comprise appropriate filter and sensing and signal processing components, to output an appropriate signal or signals for characterization or analysis of the fluid stream or its components, in connection with passage of the fluid stream through the cell assembly.

In various implementations, the multipass cell assembly may include a multipass optical reflection chamber that is configured to provide a light path length of specific desired dimensional extent, e.g., a light path length in a range of from 0.5 to 10 meters, or a light path length in a range of from 0.5 to 5 meters, or light path length of other dimensional character.

In the multipass optical reflection chamber, the inputted light may be directionally introduced, and the multipassed light may be directionally passed out of the optical reflection chamber, so that the reflected passes of light in the chamber are of a specific numeric character. The light passes are advantageously non-diametral, i.e., not directly linear in a straight-line diametral manner from the light input port to the light output port of the optical reflection chamber in a circular-shaped optical reflection chamber, in order to achieve a multipass traversal of the optical reflection chamber in which the light path segments are of chordal character so that the light impinges the reflective surface of the arcuate circumscribing member in successive passes for a suitable number of overall successive reflections.

Thus, in various embodiments, the arcuate circumscribing member may comprise a cylindrical member, and the light input structure and light output structure may be configured to produce the multipass optical reflection of light in the optical reflection chamber, wherein the multipass optical reflection of light comprises from 10 to 50 non-diametral chordal light reflections in the optical reflection chamber.

In other embodiments, the multipass cell assembly may be configured so that the multipass optical reflection of light comprises from 15 to 40 non-diametral chordal light reflections in the optical reflection chamber. In still other embodiments, the multipass cell assembly may be configured so that the multipass optical reflection of light comprises from 18 to 30 non-diametral chordal light reflections in the optical reflection chamber. Any other numbers of reflections can be employed by appropriate configuration of the multipass cell assembly.

In another aspect, the disclosure relates to a multipass cell assembly for monitoring of fluid, comprising:

a cylindrical wall member circumscribing and defining a multipass optical reflection chamber, the cylindrical wall member comprising circumferentially spaced-apart openings therein;

mirrors in the circumferentially spaced apart openings, the mirrors being inwardly facing and configured to generate multipass optical reflection of light in the multipass optical reflection chamber;

a light input structure configured to direct light from a light source onto a reflective surface of one or more of the mirrors so that said multipass optical reflection of light is generated in the optical reflection chamber;

a light output structure configured to direct multipassed light out of the optical reflection chamber for detection and processing thereof;

floor and cover members that cooperatively engage with the cylindrical wall member to enclose the multipass optical reflection chamber;

a fluid inlet configured to introduce fluid to the multipass optical reflection chamber so that it interacts with multipassing light therein, said fluid inlet comprising at least one fluid inlet port in the floor member;

a fluid outlet configured to discharge fluid from the multipass optical reflection chamber after interaction with multipassing light therein, said fluid outlet comprising at least one fluid outlet port in the floor member;

a light source mounted on the cover member and optically coupled to the light input structure; and a light detector mounted on the cover member and optically coupled light output structure.

It will be appreciated from the foregoing that the multipass cell assembly of the present disclosure may be widely varied in structure and operation to achieve efficient multipass optical reflection for extended path length interaction of inputted radiation with a fluid of interest in the optical reflection chamber.

In a further aspect, the disclosure relates to a fluid processing system, comprising:

a process tool utilizing or generating a fluid stream; and a multipass cell assembly for monitoring of fluid, as variously described herein, configured for flow of the fluid stream through the multipass optical reflection chamber from the fluid inlet to the fluid outlet for interaction with multipassing light in the multipass optical reflection chamber.

The process tool in such fluid processing system may be of any suitable type, as Employed for utilizing or generating the fluid stream that is monitored by the multipass cell assembly.

In one specific implementation, the process tool comprises a semiconductor manufacturing tool, e.g., a vapor deposition tool that is configured to deposit metal, e.g., tungsten, on a semiconductor substrate from a corresponding metal precursor, e.g., a tungsten precursor, and to generate the fluid stream comprising unreacted precursor, e.g., unreacted tungsten precursor, or unreacted tungsten precursor and vapor deposition byproducts of the tungsten precursor, resulting from the vapor deposition operation. The metal precursor for such purpose can be of any suitable type, and in various specific embodiments may comprise a metal carbonyl precursor compound, e.g., a tungsten carbonyl precursor compound.

A further aspect of the disclosure relates to a method of monitoring a fluid stream, comprising flowing the fluid stream through a multipass cell assembly of the disclosure, as variously described herein, to generate a multipassed light output, and processing the multipassed light output to characterize or analyze the fluid stream.

The light employed in such method may be of any suitable type, and in specific embodiments may comprise ultraviolet light, visible light, infrared light, or other light of desired spectral character, including combinations of the foregoing light spectra. The processing of the multipass light output to characterize or analyze the fluid stream may involve any suitable operations effective for such purpose.

For example, the processing may comprise filtering the light and impinging resulting filtered light on thermopile detection elements, to analyze chemical composition of the fluid stream. The fluid stream may comprise reactant being introduced into a semiconductor manufacturing operation, or effluent from a semiconductor manufacturing operation, e.g., a vapor deposition comprising thin-film deposition on a semiconductor substrate to deposit at least one of tungsten metal and tungsten nitride thereon from a precursor vapor of a tungsten carbonyl precursor. The method may for example be conducted, with analysis of chemical concentration and/or composition of the precursor being delivered to a vapor deposition chamber, or of the process effluent discharged therefrom, in order to control one or more process conditions of the semiconductor manufacturing operation, and/or to determine an endpoint for termination of the semiconductor manufacturing operation.

It will be recognized from the foregoing that the multipass cell assembly of the present disclosure may be constituted and implemented in a wide variety of manners, to achieve monitoring of a correspondingly wide variety of fluid screams. The fluid may comprise a gas, such term being broadly construed to include vapor. Alternatively, the fluid may comprise a liquid, or gas/liquid or vapor/liquid multi-phase fluids. Further, the fluid may comprise suspended or entrained solids, e.g., particulate contaminants or components in a fluid stream, as resulting from chemical reaction or decomposition of fluid in an upstream fluid processing operation.

The advantages and features of the disclosure are further illustrated with reference to the drawings of FIGS. 1-17 hereof.

Referring now to the drawings, FIG. 1 is a simplified schematic top plan view of a multipass cell assembly 100 of the present disclosure, in one embodiment thereof.

As illustrated, the multipass cell assembly 100 includes a main body 317, and an arcuate circumscribing member 200 that may be formed integrally with the main body, or alternatively separately formed and secured to the main body. The arcuate circumscribing member in this embodiment is of cylindrical form, comprising the support wall member 210 of cylindrical form, defining a multipass optical reflection chamber 318 circumscribed by the arcuate circumscribing member 200. The arcuate circumscribing member in this embodiment is of a cylindrical character, but it will be appreciated that in other embodiments, an arcuate circumscribing member may be employed which extends less than a full circumferentially extent around the optical reflection chamber.

The arcuate circumscribing member as illustrated has a mirror layer 300 on the support wall member 210, to provide an inwardly facing reflective surface 319 along the arcuate extent of the circumscribing member 200. The optical reflection chamber has a diameter 314 that may be of any suitable dimensional character, as appropriate to the specific optoelectronic monitoring operation that is being conducted by the multipass cell assembly.

The multipass cell assembly of FIG. 1 includes a light input structure 214 comprising a light input port 220 that may be configured for input to the optical reflection chamber of an input light beam introduced at input light angle 315. As illustrated, the input light beam 332 passes from the light input port 220 to the inwardly facing reflecting surface 319, and thereafter is successively reflected to provide multi-passing (reflected) light beams 336. In such manner, the multipassed light is outputted as output light beam 330 through the light output structure 216 comprising light output port 222. The output light structure may be configured so that the output of light is passed out of the optical reflection chamber at an output light angle 316 that is determined by the configuration of the light output structure.

Thus, the arcuate circumscribing member 200 defines a multipass optical reflection chamber 318, and the arcuate circumscribing member comprises inwardly facing reflective surface 319 along an arcuate extent thereof that generates multipass optical reflection of light impinged thereon.

The light input structure 214 is configured to direct light from a light source (not shown in FIG. 1) onto the reflective surface of the arcuate circumscribing member so that the multipass optical reflection of light is generated in the optical reflection chamber 318. The light output structure is configured to direct multipass light from the reflective surface of the arcuate circumscribing member 200 out of the optical reflection chamber 318 for detection and processing thereof, e.g., by passage to a photodetector or other optical processing component (not shown in FIG. 1).

The multipass cell assembly 100 of FIG. 1 is additionally provided with suitable fluid inlet and outlet structures (not shown in FIG. 1 for clarity) that serve to introduce fluid to the multipass optical reflection chamber so that it interacts with multipassing light therein, and to discharge fluid from the multipass optical reflection chamber after interaction with multipassing light therein, respectively. Such fluid inlet and outlet structures may be of any suitable type, and may be in a cover of the optical reflection chamber, in a floor of the optical reflection chamber, through a port in the arcuate circumscribing member, or otherwise provided to enable fluid ingress and egress to be effected, for interaction of the fluid with the light in the optical reflection chamber.

The sum effect of the multiple reflections in the optical reflection chamber of the multipass cell assembly is to extend the sample path length to achieve increased measurement sensitivity. The path length can be increased or decreased by correspondingly increasing or decreasing the diameter 314 of the optical reflection chamber, and/or by increasing or decreasing the number of internal reflections, as determined by the angles of entry 315 and output 316 from the cell assembly.

The cell assembly thus provides a compact and cost-effective design for gas monitoring cells. The internal path length provided by such design in specific embodiments may range from 0.5 m to 10 m. Path lengths outside such range may be employed, but may be constrained in specific applications by size and space requirements, and shorter path lengths may become too small to accommodate specific types of sources and detectors, depending on the specific spectral region of interest. Longer path lengths may require cell dimensions and volumes that are physically larger than desired in particular applications. Path lengths in a range appropriate for specific applications may be readily determined by modeling or empirical testing, based on the disclosure herein. In various embodiments, path lengths of 0.5 m to 5 m may be employed, to achieve appropriate sensitivity with a compact size and internal sample volume. The sample volume (i.e., the volume of the optical reflection chamber) in various embodiments may be in a range of from 10 mL to 200 mL, although sample volumes smaller or larger than those of such range may be usefully employed, in other embodiments.

The cell assembly shown in FIG. 1 may be constructed from a block of suitable material constituting the main body 317, in which a cavity is cut with a circular cross-section section to form the optical reflection chamber 318. The block may be formed of any appropriate material of construction, such as metal, ceramic, polymer, compounds of materials, etc. The surface of the walls bounding such circular cross-section section optical reflection chamber may in specific embodiments be polished to a mirror quality finish to provide the inwardly facing reflective surface 319. Top and bottom plates may be added to provide a circular cross-section section cavity that is bounded by the top and bottom plates and by the arcuate circumscribing member 200 with the mirror layer 300 thereon, which as indicated may be a layer of the integrally formed wall member 210. The top and bottom plates may be mirror polished as well, to provide a cavity that behaves as a light conduit as well as producing the multiple reflections necessary to generate the extended optical path length.

Various configurations of the multipass cell assembly are possible, as regards the placement and positioning of the light input structure and light output structure.

Figure 2:
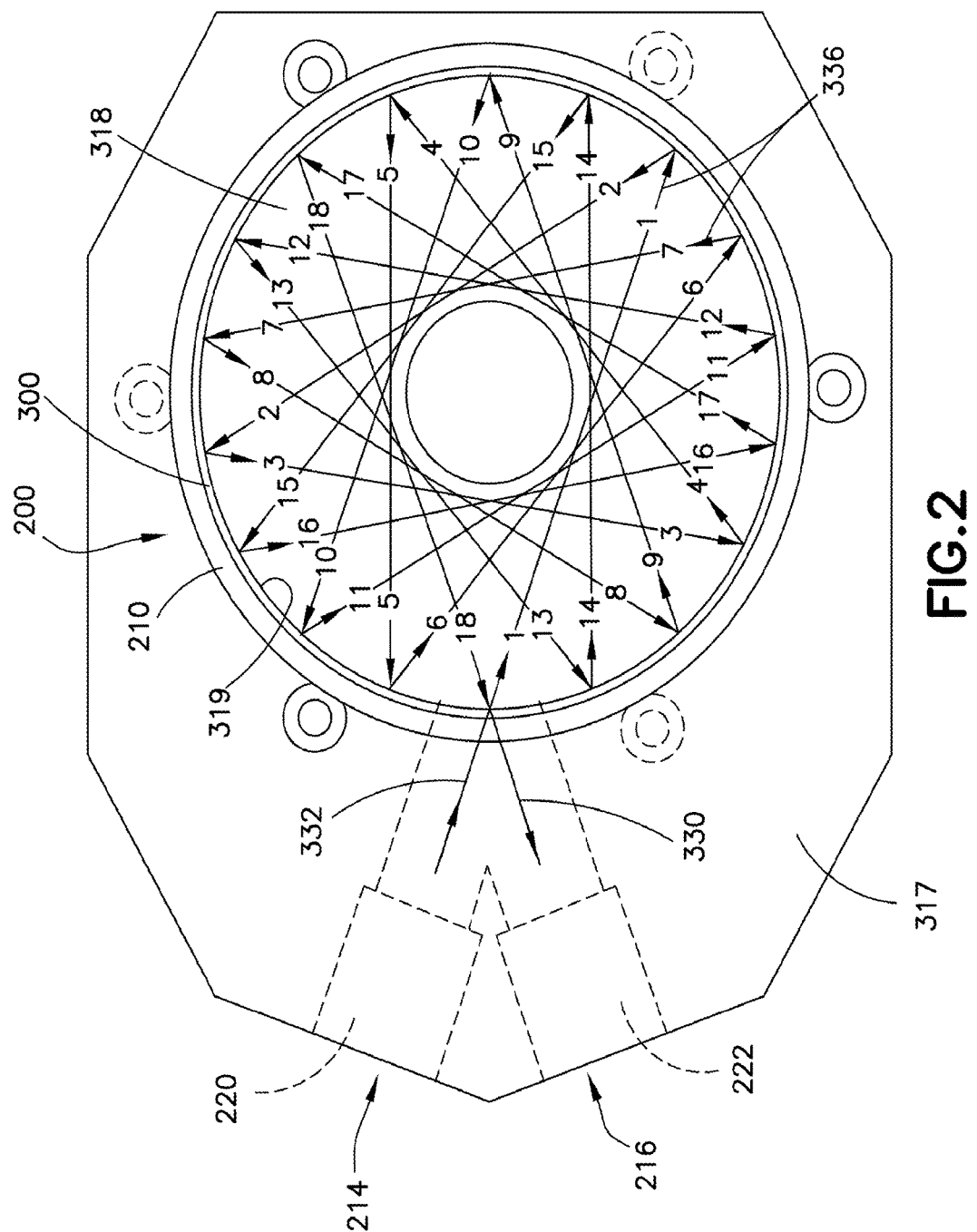
FIG. 2 is a simplified schematic top plan view of a multipass cell assembly of the present disclosure, according to another embodiment thereof.

FIG. 2 is a simplified schematic top plan view of a multipass cell assembly of the present disclosure, according to another embodiment thereof. The reference numerals of the corresponding parts and elements of the FIG. 2 multipass cell assembly are correspondingly numbered with respect to the same parts and elements of FIG. 1. The FIG. 1 multipass cell assembly includes input and output light structures 214 and 216, respectively, which are circumferentially spaced apart from one another, e.g., by an angle of 60-75°. In contrast, the input and output light structures 214 and 216 in the FIG. 2 multipass light assembly are positioned in close proximity to one another, being circumferentially spaced apart by an angle that may be on the order of 30-45°.

Figure 3:
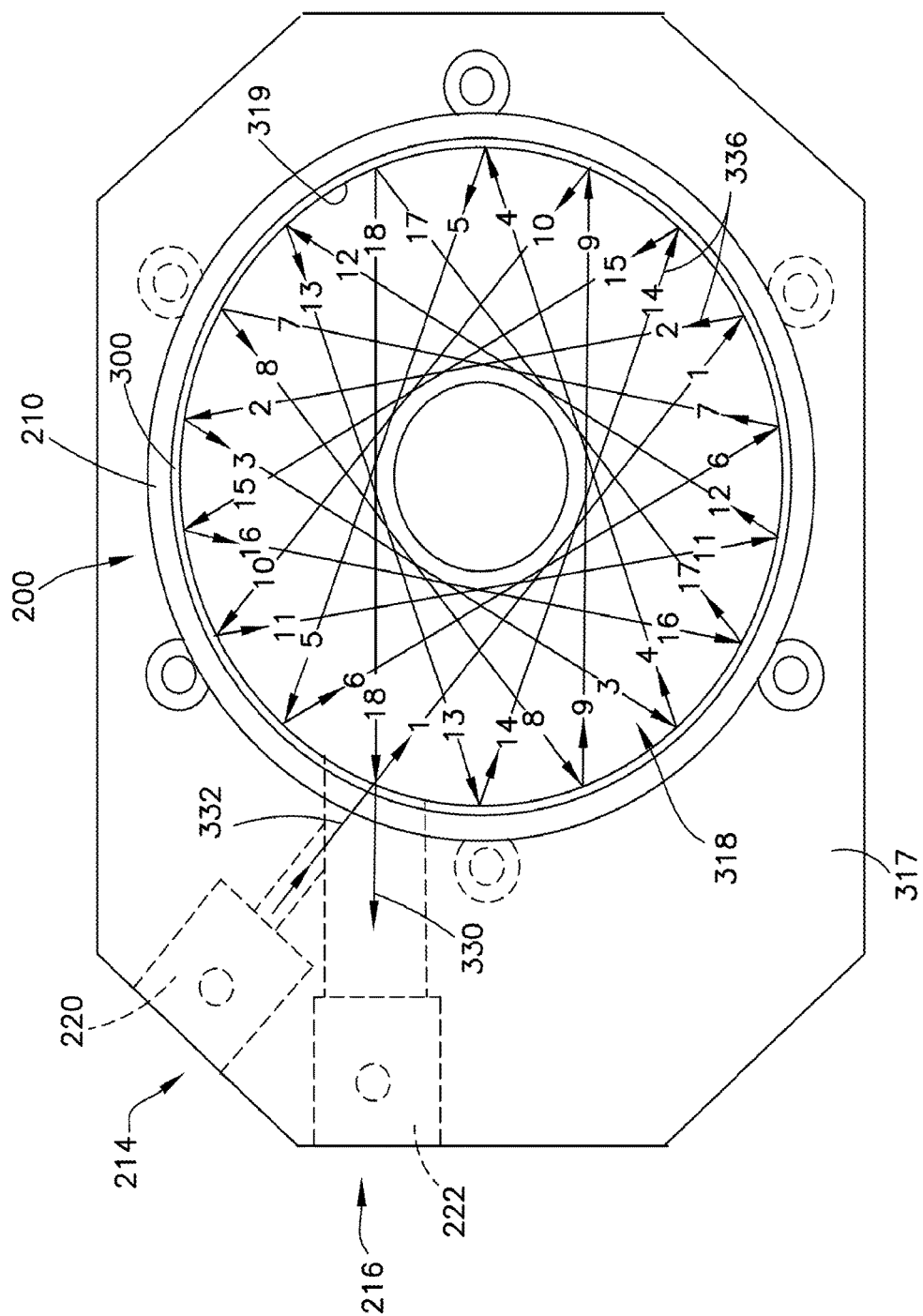
FIG. 3 is a simplified schematic top plan view of a multipass cell assembly of the present disclosure according to a still further embodiment thereof.

FIG. 3 is a simplified schematic top plan view of a multipass cell assembly of the present disclosure according to a still further embodiment thereof, in which the parts and elements are numbered correspondingly with respect to those of the FIG. 1 multipass cell assembly. In the multipass cell assembly of FIG. 3, the light input and output structures are likewise in close proximity, with the light input structure 214 having an associated light input passage that intersects the light output passage of light output structure 216.

Figure 4:
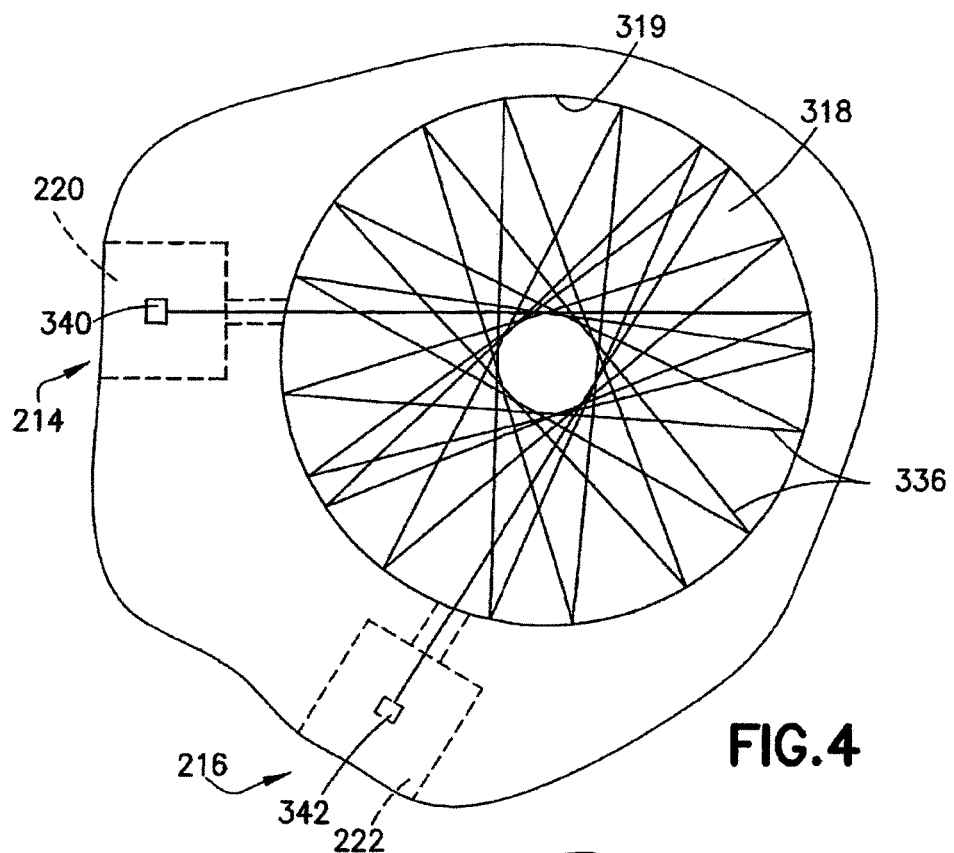
FIG. 4 is a simplified schematic top plan view of a multipass cell arrangement according to yet another embodiment of the disclosure.

FIG. 4 is a simplified schematic top plan view of a multipass cell arrangement according to yet another embodiment of the disclosure, in which the parts and elements are numbered correspondingly with respect to the parts and elements of FIG. 1. In the FIG. 4 multipass cell assembly, a light source element 340 is positioned in the light input port 220 of the light input structure 214, and a light detector element 342 is disposed in the light output port 222 of the light output structure 216. In a specific implementation of this embodiment, 20 multipass reflections may be generated to provide a path length of 1 m.

Figure 5:
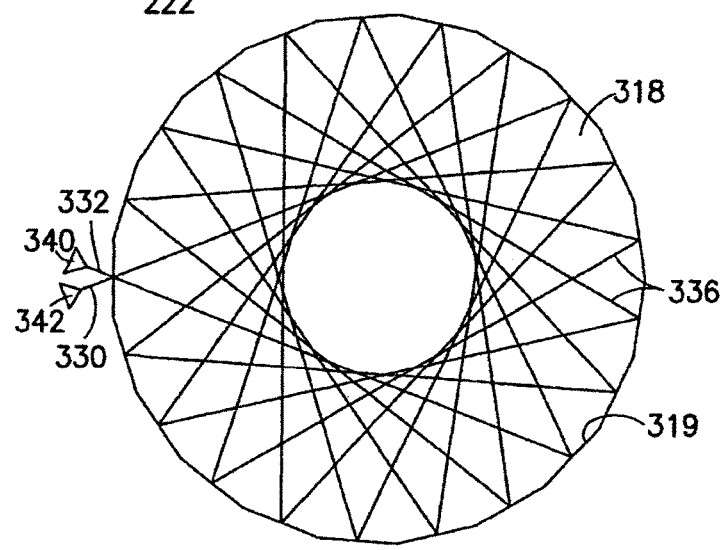
FIG. 5 is a simplified schematic top plan view of a multipass cell arrangement employing faceted reflective surfaces, according to a further embodiment of the disclosure.

FIG. 5 is a simplified schematic top plan view of a multipass cell arrangement employing faceted reflective surfaces, according to a further embodiment of the disclosure, in which corresponding parts and elements are numbered correspondingly to those of FIG. 1. In this embodiment, the inwardly facing reflective surface 319 bounding the optical reflection chamber 318 is constituted by faceted wall surface, and a light source 340 and a light detector 342 are employed. As an illustrative example, such system in a specific embodiment may be configured to provide 21 reflections in the optical reflection chamber, generating a corresponding path length of 1.03 m.

In the foregoing embodiments of FIGS. 1-5, the number of reflections from the wall surfaces of the optical reflection chamber is controlled by the angle employed to input the source radiation. The overall path length of the cell is governed by the number of reflections times the diameter of the internal cavity, and the height of the internal cavity is set to be compatible with the dimensions of the source radiation and the geometry of the radiation beam at its point of exit from the cell. In specific embodiments, the beam geometry may be adapted for interfacing to a specific type of instrument by the provision of auxiliary optics, including focusing lenses.

The overall size of the multipass cell assembly may be widely varied. In some embodiments, the cell may be micro-machined to provide miniaturized or small-scale gas sampling systems. In such cases, light source components will be employed that produce highly collimated, micro-cross-section beams of micron or sub-micron size. The multipass cell assembly in various implementations may be utilized for spectral gas measurement systems on an integrated circuitry chip, or otherwise for small-scale or nano-scale implementations.

Figure 6:
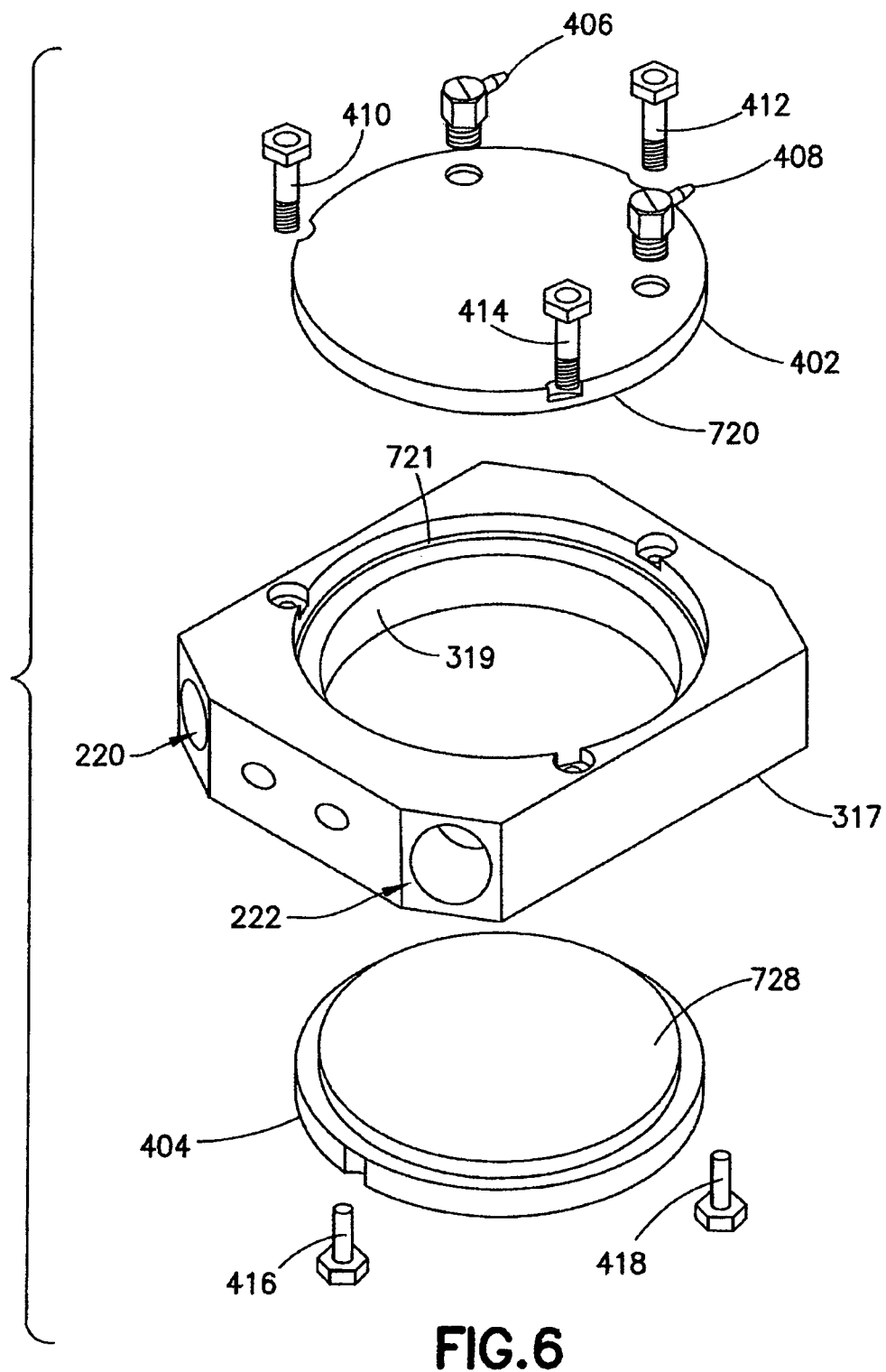
FIG. 6 is an exploded perspective view of a multipass cell assembly according to a still further embodiment of the disclosure.

FIG. 6 is an exploded perspective view of a multipass cell assembly according to a still further embodiment of the disclosure. In the FIG. 6 multipass cell assembly, corresponding parts and elements to those illustratively described in FIGS. 1-5 are correspondingly numbered.

The FIG. 6 assembly comprises a cavity body 317 featuring a plated minor surface 319 circumscribing the optical reflection chamber. The chamber is also circumscribed by an O-ring seal element 721, to achieve leak-tight sealing of the optical reflection cavity with the top cover 402. A similar O-ring sealing element (not shown in FIG. 6) is provided at the bottom portion of the chamber, for leak-tight sealing of the optical reflection cavity with the bottom cover 404.

The cavity body 317 is provided with longitudinally extending mechanical fastener openings to accommodate shoulder bolts 410, 412, and 414 securing the top cover 402 in place, and shoulder bolts 416 and 418 securing the bottom cover 404 in place. The block is provided with an inlet port 220 accommodating input of light from an input light source (not shown in FIG. 6), and the block also includes a light output port 222 to accommodate output of light to a light detector (not shown in FIG. 6).

The top cover 402 of the FIG. 6 multipass cell assembly is provided with a polished plated surface 720, and the bottom cover 404 likewise is provided with a polished plated surface 728, to enhance the optical reflective character of the optical reflection cavity bounded by the top and bottom covers and the plated minor surface 319 of the optical reflection cavity.

In the FIG. 6 assembly, a fluid inlet 406 and a fluid outlet 408 are provided in the top cover, to provide for introduction of fluid, in inlet 406, to the optical reflection chamber for interaction with light therein, and for discharge of fluid, in outlet 408, after fluid interaction with the multipassing light in the optical reflection chamber.

The multipass cell assembly of the present disclosure may be utilized for measurement and/or characterization of gases and vapors, as well as other fluids, including liquids and liquid/gas and liquid/vapor material, and solid/vapor material. The spectral region of light interaction with the fluid may be in any suitable range of wavelengths, or a specific wavelength, in the electromagnetic radiation spectrum. In specific applications, the light utilized for measurement and/or characterization of the fluid may be ultraviolet light, visible light, near-infrared light, infrared, mid-infrared, or other specific spectral regime or wavelength range, including mixtures of different types of radiation for detection or characterization of specific material, e.g., fluids or fluid components.

Applications contemplated for multipass subassemblies of the present disclosure are of widely varying type. For example, assemblies of such type may be employed for measurement of low levels of chromophores in UV and visible spectral regions, including the detection and monitoring of low concentrations of organic materials in water samples. Liquid compositions may be monitored by short wave near-infrared measurements, utilizing path lengths that may for example be on the order of 5 cm to 20 cm or more.

The optical reflection chamber of the assembly can be utilized for measurement of low levels of fluorescence, phosphorescence, or chemiluminescence, with longitudinal excitation down the axis of the cell. In liquid applications, the optical reflection chamber can for example be configured as a polished metal wall cavity that is used for applications in which the fluid of interest does not foul, contaminate, or attack the metallic material. In applications utilizing fluids having potential interaction with metal materials of construction, the optical reflection chamber may be formed of a polymer, glass, or quartz material, or may be coated with a reflective surface material on the exterior wall of the cell, to provide appropriate reflectivity while at the same time protecting the underlying metal from attack.

The optical reflection chamber may be configured as a cylindrical chamber, or as a tubular chamber, or it may be configured in other manner that is appropriate to the specific application, accommodating multipass operation of the chamber to achieve extended path length for monitoring of a specific fluid.

The multipass cell assembly of the present disclosure thus may be used for interaction of fluid with light, involving absorption, as well as for other forms of optical spectroscopy. The cell assembly may utilize a cavity formed with polished, generally vertically extending surface and with its top and bottom sealed by flat polished surfaces to form a totally reflective cavity. Light may be introduced into the cavity through a circular cross-section aperture in the vertically extending surface so that it is directed across the cavity to the opposing surface, with an incident angle being such that the light reflects from the wall at a different angle to the angle of the incoming light beam, to initiate a continuous path of multiple reflections from the enclosing vertical reflective surface of the cavity, with the light ultimately exiting the cavity of the second aperture in the vertically extending surface. The light/radiation interacts with the fluid sample during the multiple reflections within the cavity, and the effective path length is determined by the number of total wall-to-wall reflections within the cavity, and the distance traveled between successive reflections, which in turn is governed by the distance between opposing surfaces within the cavity, and the input and exit angles of the respective light/radiation input and output apertures.

The cavity may be provided in the form of a circular cross-section chamber constituting an internal reflective area defined by the cylindrical circumscribing surface from which light/radiation is reflected. As indicated above, the cavity may be enclosed by continuous, planar reflective surfaces such as plates at the respective top and bottom extremities of the cell cavity.

The respective apertures for the light source and light detector components may be machined or drilled into the walls of the cell, to provide respective circular cross-section section openings to accommodate respective light source and detector devices, or alternatively, mirrors, optical fiber arrays, or other components optically coupling the light inlet and outlet apertures with respective source and detector devices may be employed. The apertures can be of appropriate dimensional character to define the initial diameter of the light beam that is inputted to the optical reflection cavity, or the light beam that is outputted from the optical reflection cavity. The diameters of the light input and output beams can be the same as, or different from, one another, dependent on the degree of beam divergence or convergence within the cell.

The nominal or mean path length of the cell is determined by the relative angles between the input and output apertures in the wall of the cell, in the horizontal plane, relative to the base of the cell, and the diameter across the cylindrical cross-section section of the cell. Parallelism of opposing wall surfaces in the cavity is utilized to ensure optimal reflection geometry within the cell. Reflective internal surfaces of top and bottom enclosing members of the cell assist in correcting vertical deviations of the light beam and forming a light pipe-like structure in the cell.

The cell may be provided with two or more ports for the input and output of the material (e.g., gas, vapor, liquid, etc.) being monitored in the cell. The ports may be located in a top and/or bottom plate (or in a side wall), as openings that may be machined in such structural components of the cell. A continuous seal, such as provided by an O-ring of suitable elastomeric composition, or other form of mechanical seal, may be employed to effect a fluid-tight character of the optical reflection cavity. For example, grooves or recesses may be cut in a main body portion of the cell, to accommodate O-rings of such type, for sealing of the cavity bounded by such top and bottom plates. A seal of appropriate character may be employed to support vacuum, atmospheric pressure, or superatmospheric pressure of the fluid in the cell.

The circumscribing wall of the optical reflection cavity may comprise a machined or molded continuous surface defining a circular cross-section of the cavity. Alternatively, the reflective wall surface may be faceted, segmented, or otherwise shaped to provide an appropriate reflective(/focusing) surface for multipass light transmission in the cavity. The surfaces may be machined or otherwise configured to provide an appropriate degree of divergence or convergence of the reflected beam. The light input structure may be configured so that incoming light strikes the center of an opposing faceted area of the circumscribing wall, so that the beam is multiply internally reflected from facet to facet of a multifaceted wall, until the beam exits as a reflection from a facet surface, through the exit aperture of the output structure.

The light input structure may be configured to provide a collimated beam of radiation to the optical reflection cavity, with the exit beam being collimated or close to collimated in character, dependent on the geometry of the internal reflective wall surface. The cell may be employed with any suitable detection/analysis instruments, e.g., photometers, spectrophotometers, spectrometers and other optical analyzers. The multipassed beam exiting the optical reflection cavity may, if necessary or desired, be processed with appropriate imaging optics for transmission to the detector system of the instrument, or its photometric or spectrographic equivalent.

Appropriate source and detector devices may be closely coupled to the multipass cell without the need of any external focusing optics, to constitute a fully integrated fluid monitoring system. The source device may be provided adjacent to or within the light/radiation input aperture. In like manner, the light/radiation detector may be provided adjacent to or within the light/radiation output aperture. The respective light/radiation input and output apertures may be provided with windows to provide an appropriate seal to the optical reflection cavity. Windows for such purpose may be constructed of suitable material that is rigid, inert to the sample being monitored and to the ambient operating environment, and transparent in the spectral region of interest. Coatings may be employed on either or both faces of windows to enhance chemical inertness and/or to reduce reflection losses at either optical surface. Windows may be retained in position by mechanical seal elements, e.g., O-rings or equivalents, by sealants, adhesive bonding media, soldering, or other bonding or securement technique and material.

The cell can be fabricated of any suitable material of construction, dependent on the physical and chemical requirements of the monitoring application, the chemical reactivity of the fluid medium, regulatory requirements, operating environment, cost considerations, etc. The cell may for example be made from a metal such as aluminum, stainless steel, or a special alloy as required to meet applicable standards of chemical inertness. The optical surfaces of the internal cavity may be provided by suitable polishing and/or cutting procedures, such as diamond turning. The reflectivity of the cut/polished surface can be enhanced by deposition of reflective material, such as gold, nickel, dielectric material, etc.

The cell may also be formed of metal or other suitable material of construction, by a casting or molding technique, with subsequent polishing of the optical surfaces. Materials of construction such as ceramics, engineering polymers, or other polymers or resins (thermoplastic, thermosetting, or catalytically cured) are contemplated, optionally with enhancement of reflectivity of optical surfaces by deposition of reflective metal or dielectric material. The cell cavity walls may be formed in segments by molding, casting, or other techniques, for subsequent assembly of a composite wall structure, which may be faceted or otherwise shaped or contoured for suitable reflective character in use of the cell. The wall segments in such composite wall structures may be assembled with bonding by suitable adhesive or sealant materials.

The cell may be fabricated of thermally conductive material and incorporate heat transfer components or capability, so that the interaction of the light/radiation with the fluid in the cell is conducted at specific temperature. For this purpose, the cell may be fabricated so that isothermal operation is insured, with the temperature of the cavity at all points within the optical reflectance chamber being closely uniform. Heater elements or heat transfer passages may be provided in the cavity wall and/or cover members for such purpose.

Figure 7:
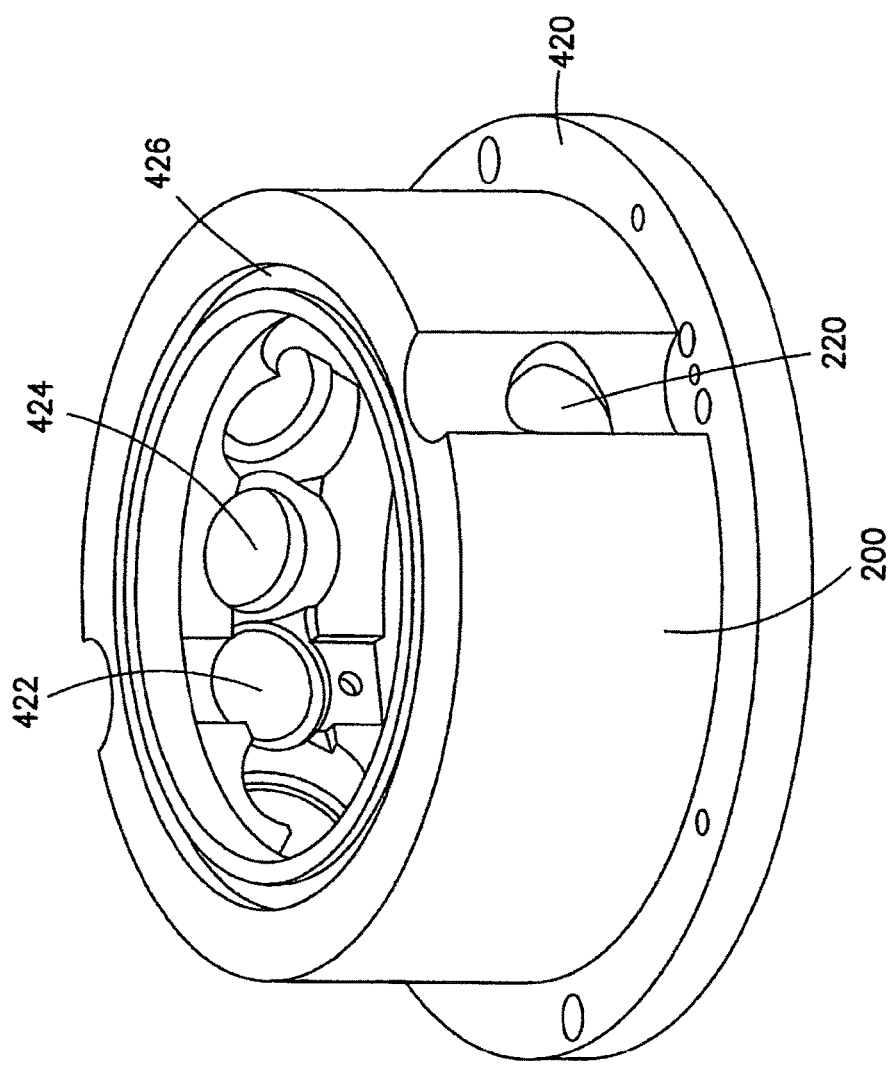
FIG. 7 is a perspective schematic view of a multipass cell subassembly according to one embodiment of the disclosure.

FIG. 7 is a perspective schematic view of a multipass cell subassembly according to another embodiment of the disclosure. This cell subassembly includes a floor mounting flange 420 from which upwardly extends an arcuate circumscribing member 200 in the form of a cylindrical wall configured with a light input port 220 therein, as shown.

The cylindrical wall includes a series of receiving openings 422 therein along the circumferential extent of the wall, intermediate its upper and lower extremities, which include the light input port and the light output port openings. In the receiving openings, other than the openings for the light input port and light output port, are disposed mirrors 424 for generating reflective passes of the radiation impinged thereon. At the upper end of the cylindrical wall is provided an O-ring receiving groove 426, accommodating insertion therein of an O-ring for sealing of the optical reflection chamber.

Figure 8:
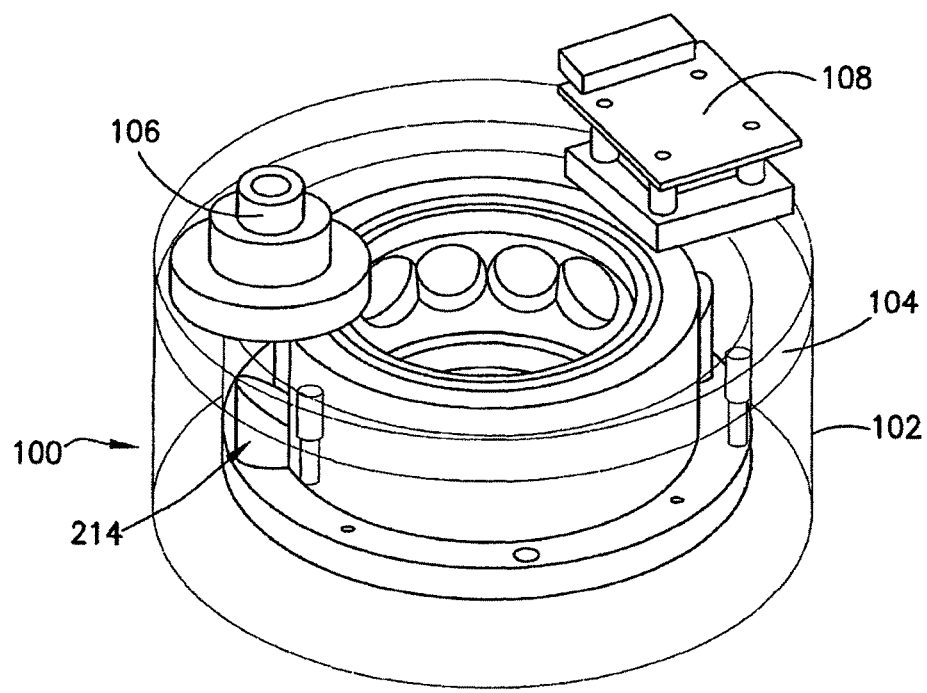
FIG. 8 is a perspective schematic view of a multipass cell assembly including the subassembly of FIG. 7.

FIG. 8 is a perspective schematic view of a multipass cell assembly including the subassembly of FIG. 7. The multipass cell assembly 100 includes the light input structure 214 and the associated light source 106, and light detector 108. The cell assembly comprises housing 102 and cover member 104.

Figure 9:
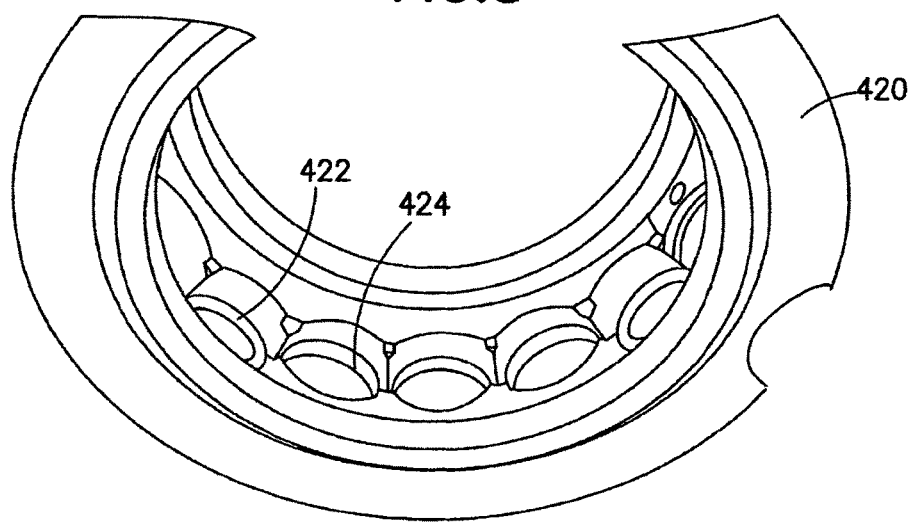
FIG. 9 is a bottom perspective view of the multipass cell subassembly of FIG. 7.

FIG. 9 is a bottom perspective view of the multipass cell subassembly of FIG. 7, showing the floor mounting flange 420, receiving openings 422, and mirrors 424.

Figure 10:
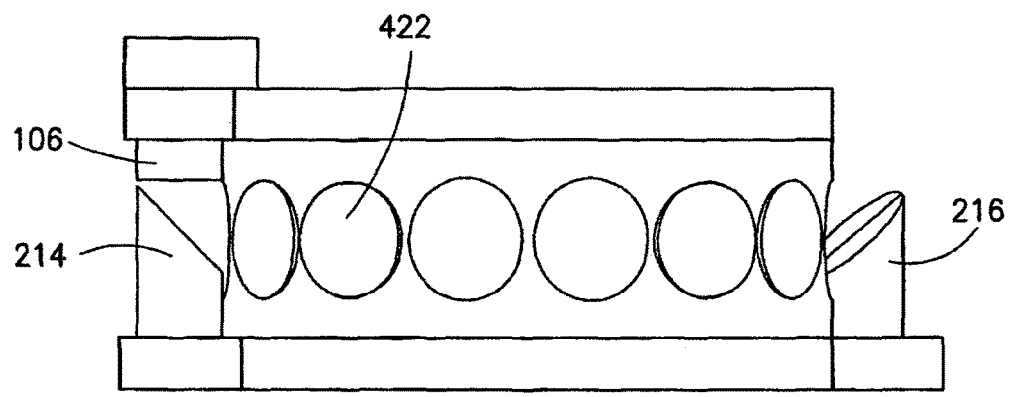
FIG. 10 is a schematic elevation view of the multipass cell subassembly of FIG. 9.

FIG. 10 is a schematic elevation view of the multipass cell subassembly of FIG. 9. As illustrated, the light source 106 is arranged in relation to the light input structure, to introduce an input light beam into the optical reflection chamber. The receiving openings 422 of the cell subassembly are illustrated, together with the light output structure 216, which receives the output light beam from the optical reflection chamber and directs such beam to the detector of the assembly.

Figure 11:
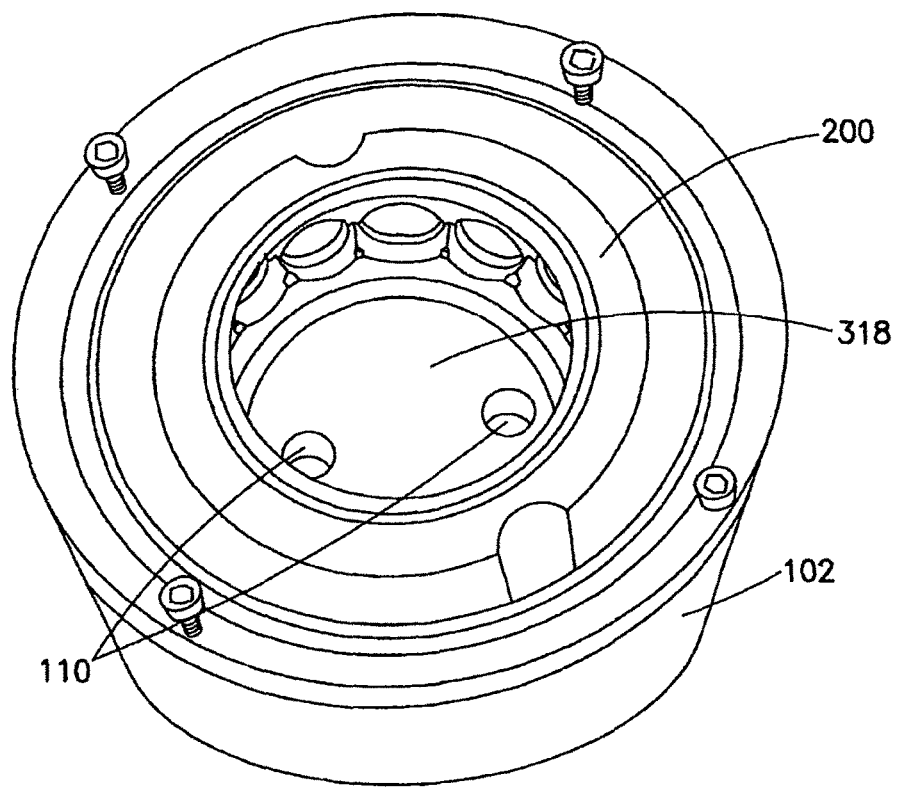
FIG. 11 is a top perspective view of a multipass cell assembly, showing the details of gas inlet structure therein.

FIG. 11 is a top perspective view of a multipass cell assembly, showing the details of the fluid inlet structure therein. As illustrated, the arcuate circumscribing member 200 circumscribes the optical reflection chamber 318 in the cell assembly housing 102, and fluid inlet(/outlet) ports 110 are provided for introducing fluid into the optical reflection chamber for flow therethrough.

Figure 12:
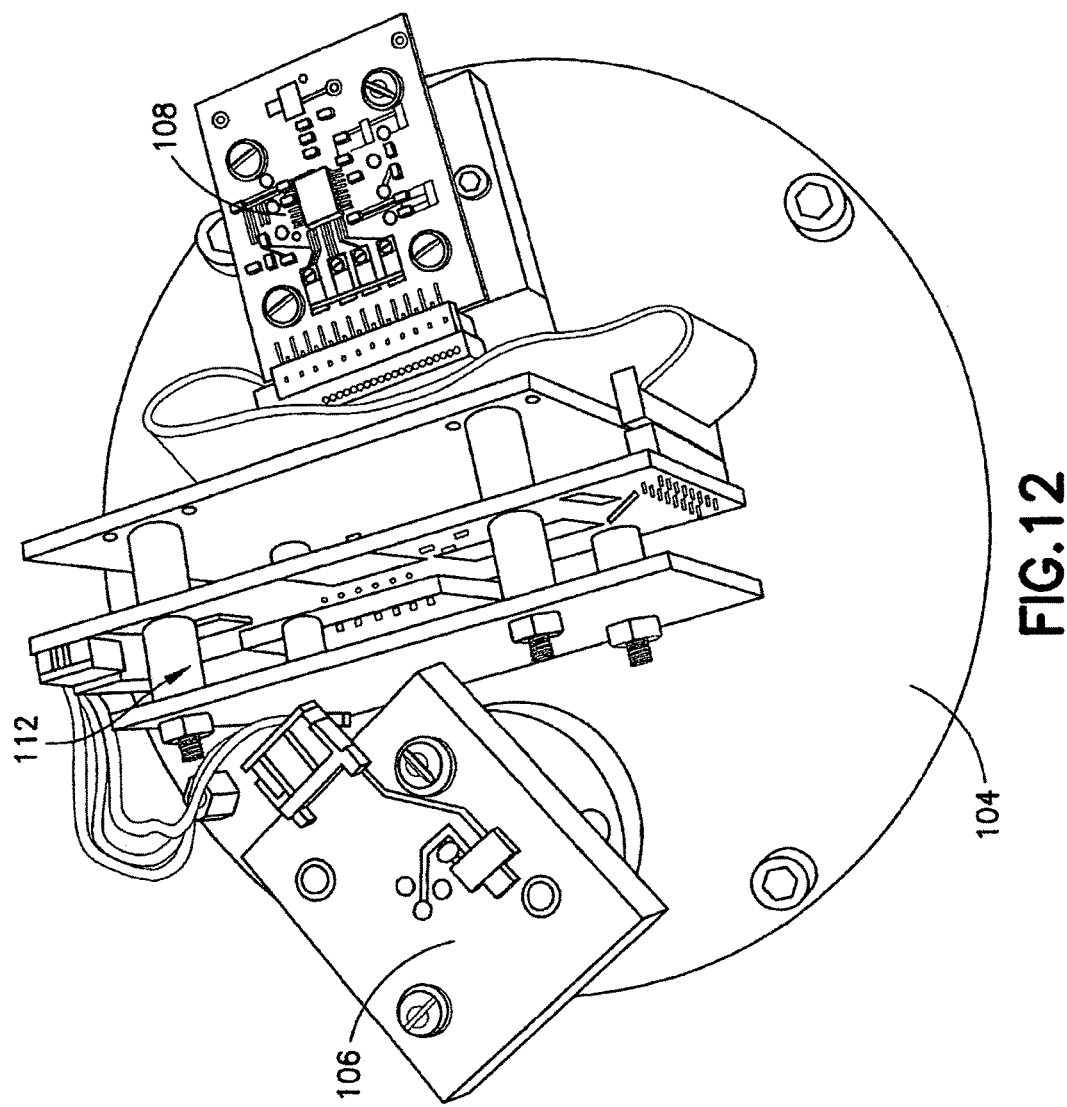
FIG. 12 is a top perspective view of a multipass cell assembly according to one embodiment of the disclosure, featuring a cell assembly cover-mounted IR source and IR detector.

FIG. 12 is a top perspective view of a multipass cell assembly according to one embodiment of the disclosure, featuring a cell assembly including a cover-mounted IR source and a cover-mounted IR detector.

The cell assembly cover member 104 shown in FIG. 12 has mounted thereon a light source 106 and a light detector 108, with an electronics module 112 therebetween, for carrying out the monitoring operation and generating a monitoring output signal.

Figure 13:
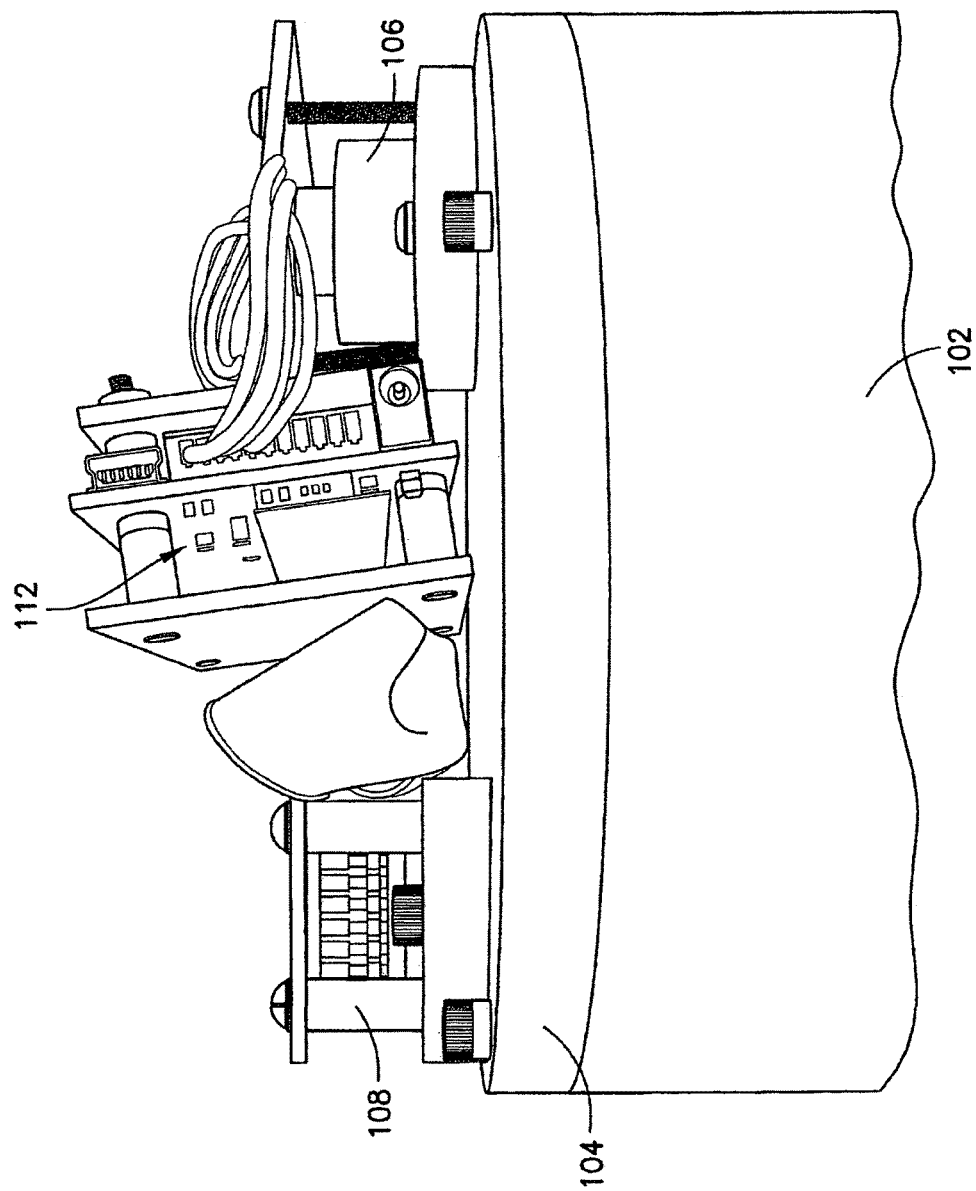
FIG. 13 is an elevation view of the multipass cell assembly of FIG. 12.

FIG. 13 is an elevation view of the multipass cell assembly of FIG. 12. As illustrated, the cell assembly housing 102 engages the cell assembly cover member 104, and the cover member 104 has mounted thereon the light source 106, light detector 108, and an associated electronics module 112.

Figure 14:
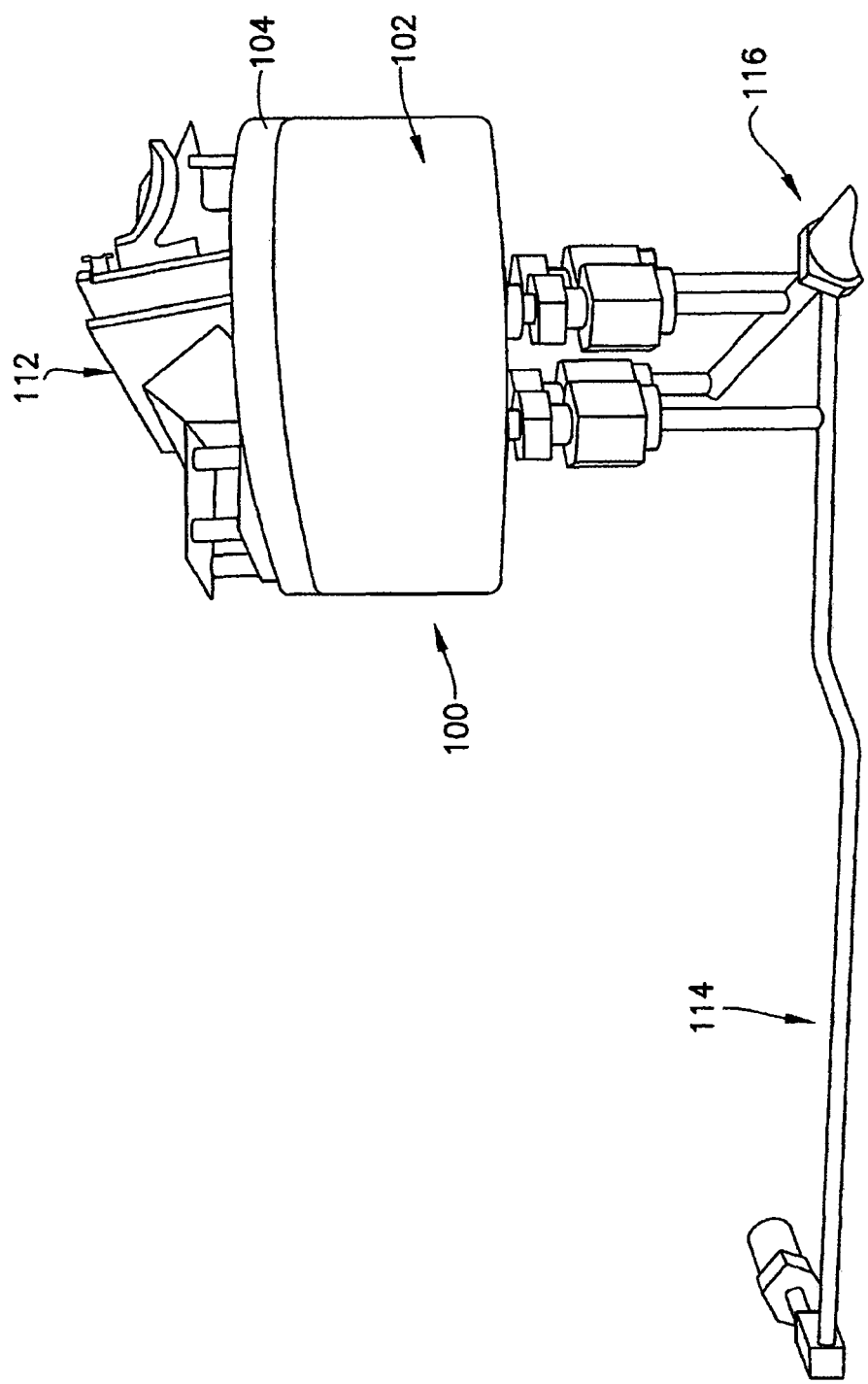
FIG. 14 is a perspective view of a multipass cell assembly of the type shown in FIGS. 12 and 13, further including gas flow circuitry including gas inlet and outlet lines coupled to the multipass cell.

FIG. 14 is a perspective view of a multipass cell assembly of the type shown in FIGS. 12 and 13, further including gas flow circuitry including gas inlet and outlet lines coupled to the multipass cell. The gas flow circuitry includes gas inlet lines 114, as manifolded for introduction of fluid through the floor of the optical reflection chamber within cell assembly housing 102, via spaced-apart fluid inlet ports in the floor of the chamber. A gas outlet line 116 is provided for discharge of fluid from the optical reflection chamber after its interaction with the multipassing light therein.

Figure 15:
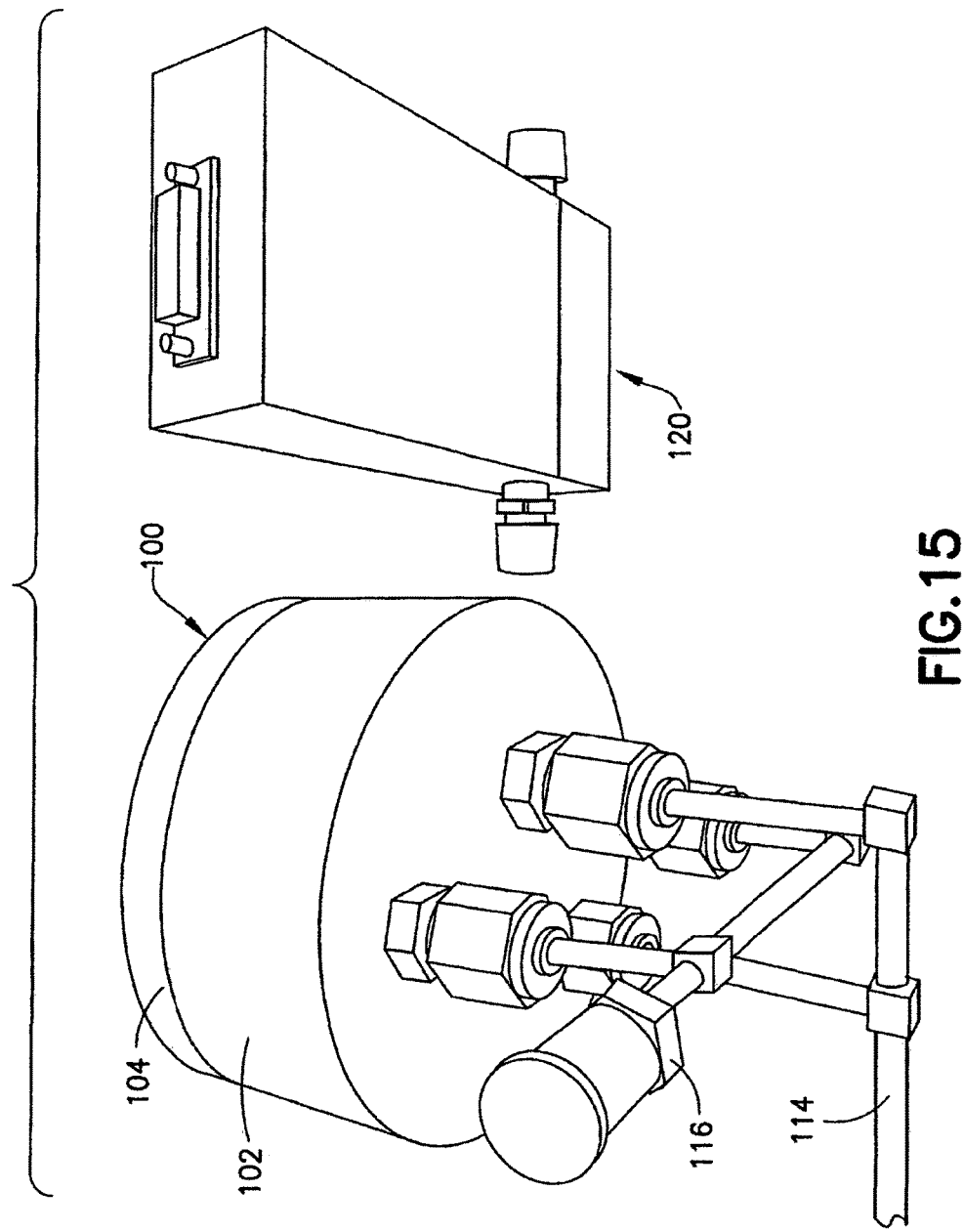
FIG. 15 is a perspective view of the multipass cell assembly of FIG. 14, shown with a mass flow controller, to indicate the dimensional size characteristics of the multipass cell assembly.

FIG. 15 is a perspective view of the multipass cell assembly 100 of FIG. 14, shown with a mass flow controller 120, to indicate the relative dimensional size characteristics of the multipass cell assembly.

Figure 16:
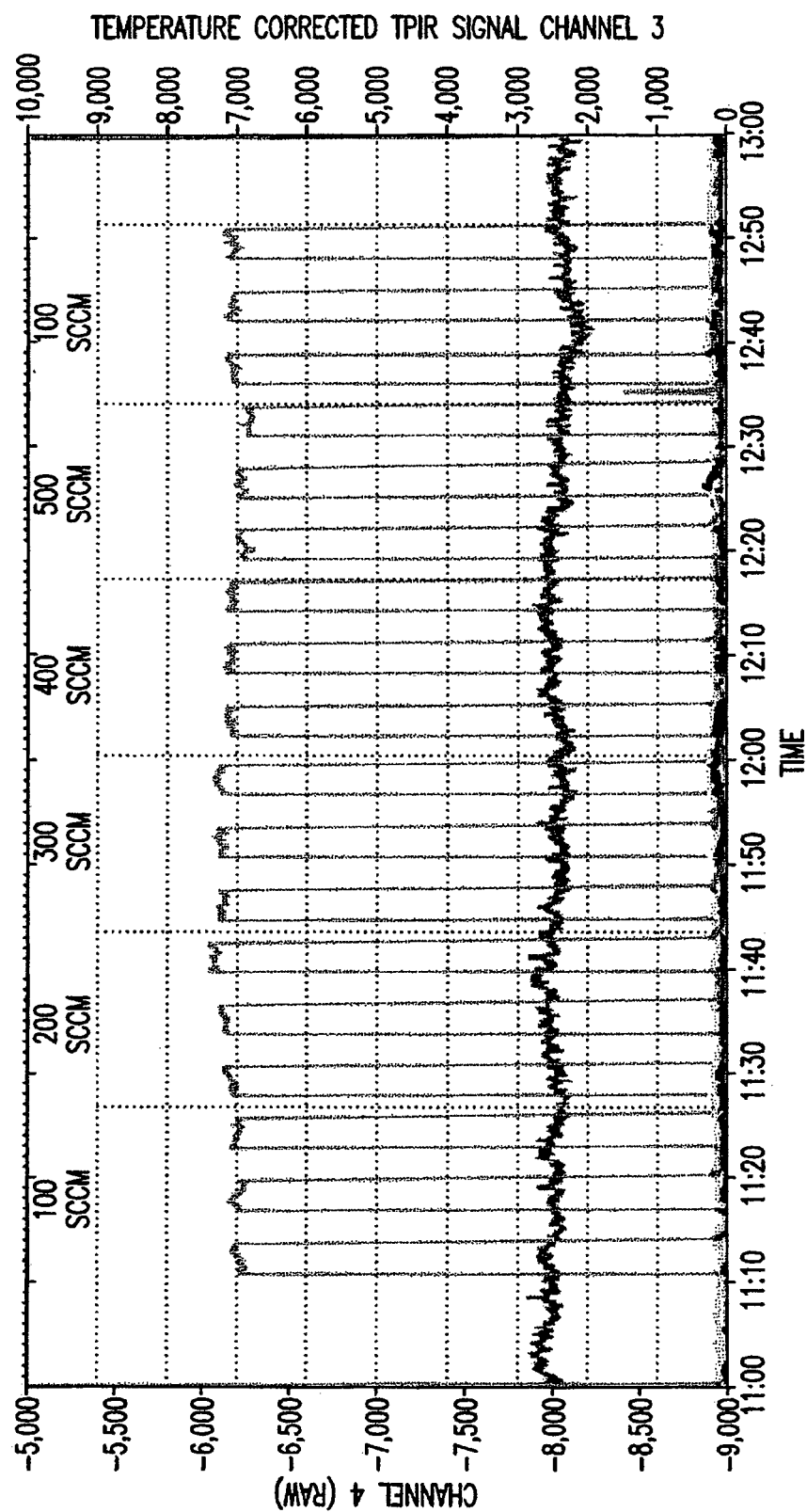
FIG. 16 is a graph of output data as a function of time for a multipass cell assembly monitoring a vapor stream including vapor from a vaporizer supplying a tungsten carbonyl precursor vapor, and argon carrier gas, as representative of a vapor stream used for tungsten thin-film deposition on a semiconductor substrate in a vapor deposition operation.

FIG. 16 is a graph of output data as a function of time for a multipass cell assembly monitoring a vapor stream including vapor from a vaporizer supplying a tungsten carbonyl precursor vapor, and nitrogen carrier gas, as representative of a vapor stream used for tungsten metallization of a semiconductor substrate in a vapor deposition operation.

The vaporizer utilized to generate the data of FIG. 16 was operated in a pulsed flow format, at temperature of 55° C., and pressure of 40 torr, for delivery of the tungsten carbonyl precursor vapor in a combined argon/nitrogen carrier gas stream, at an argon carrier gas flow rate of 500 sccm and a nitrogen carrier gas flow rate of 50 sccm. The consolidated vapor including the carrier gas and the tungsten carbonyl precursor vapor was flowed to a multipass cell assembly according the present disclosure, in which the multipass cell assembly included a 4-channel infrared detector. The radiation inputted to the optical reflection chamber of the cell assembly was infrared radiation.

The first channel of the four-channel detector monitored carbon monoxide (CO), indicated by the blue line , the second channel monitored carbon dioxide ($CO_2$), indicated by the magenta line , the third channel monitored the tungsten carbonyl precursor, indicated by the green line , and the fourth channel was a reference channel, indicated by the red line .

The data of the FIG. 16 graph indicate that the multipass cell assembly was highly effective in characterizing the composition of the gas stream with respect to CO, $CO_2$, and the tungsten carbonyl compound, and in showing the performance quality of the vaporizer providing the tungsten carbonyl precursor vapor.

Figure 17:
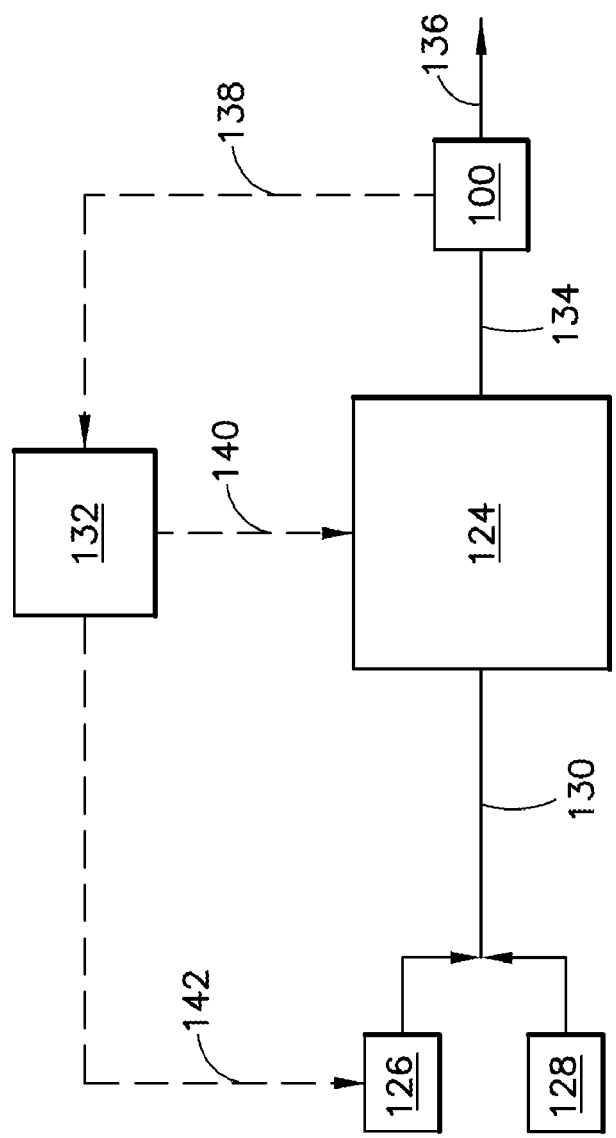
FIG. 17 is a schematic representation of a semiconductor manufacturing process system, utilizing a multipass cell assembly of the present disclosure, in connection with a control system for modulating system operation in response to multipass cell assembly sensing.

FIG. 17 is a schematic representation of a semiconductor manufacturing process system, utilizing a multipass cell assembly of the present disclosure, in connection with a control system for modulating system operation in response to multipass cell assembly sensing.

The multipass cell assembly 100 is located downstream (or it may alternatively be located upstream) of a vapor deposition tool 124, which may for example comprise a chemical vapor deposition process chamber provided in a semiconductor manufacturing facility.

The vapor deposition tool 124 in this process system is arranged to receive precursor vapor from a precursor source vessel 126 and carrier gas from a carrier gas source vessel 128. The respective precursor and carrier gas streams are combined to form a precursor gas mixture that is flowed in precursor gas mixture feed line 130 to the vapor deposition tool. The vapor deposition process conducted in the vapor deposition tool 124 produces an effluent that is discharged from the tool in effluent discharge line 134 and passes to the multipass cell assembly 100. The effluent gas is monitored in the multipass cell assembly and discharged from such assembly as final effluent in vent line 136.

The multipass cell assembly 100 monitors the effluent gas and generates a corresponding output that is transmitted in output signal transmission line 138 to central processor unit (CPU) 132. The CPU 132 may be programmatically arranged to process the output signal from output signal transmission line 138, and to responsively generate correlative control signals that are outputted in control signal transmission line 140 and control signal transmission line 142. In such arrangement, the control signal in line 140 is employed to modulate the operation of the vapor deposition tool 124, and the control signal in line 142 is employed to modulate the supply of precursor and carrier gas from the respective precursor and carrier gas vessels 126 and 128.

By this arrangement, the process conditions in or associated with the vapor deposition tool 124 may be controllably adjusted to maximize deposition of tungsten on the substrate being metallized in the tool, while concurrently avoiding unwanted side reactions of the precursor vapor that could otherwise produce an undesired level of solid particulates or other contaminants. The control signal in signal transmission line 142 may correspondingly be used to adjust the concentration of precursor in the precursor gas mixture flowed in line 130 to the tool, e.g., by modulating flow control valves associated with the vessels 126 and 128, to thereby achieve the desired concentration of precursor in the precursor gas mixture.

The multipass cell assembly, in addition to its utilization for process control purposes, may also be employed to detect an endpoint of the process operation, or a condition of approaching exhaustion of the supply vessels containing precursor and carrier gas, and to correspondingly terminate operation of the process. The CPU 132 for such purpose may comprise any suitable processor components and configuration, and may for example comprise a special purpose computer that is programmed for monitoring and control of the process system, utilizing the multipass cell assembly. Alternatively, the CPU may comprise microprocessors, programmable logic controllers, or other controller component(s).

It will be appreciated from the foregoing that the multipass cell assembly of the present disclosure may be usefully employed in a wide variety of fluid monitoring operations and applications, to achieve extended path length radiation-based monitoring of fluids and fluid-containing materials, and that the multipass cell assembly in consequence of the structural arrangements herein described can be deployed in extremely compact forms, as desirable in applications such as semiconductor manufacturing, in which the footprint and volume of process components are desirably minimized. It will also be apparent from the foregoing discussion that the multipass cell assembly of the present disclosure is of comparatively simple form, and amenable to cost-effective manufacture, assembly, installation, and operation.

The multipass cell assembly of the present disclosure may advantageously be used in various embodiments to monitor selected gas components of process streams that are supplied to gas-utilizing equipment in process systems. An example is the use of such a multipass cell assembly to monitor tungsten hexacarbonyl, $W(CO)_6$, supplied in a process gas stream to a vapor deposition tool in a manufacturing process system for deposition of tungsten on a substrate. The vapor deposition tool in such application may for example comprise a chemical vapor deposition (CVD) process tool or an atomic layer deposition (ALD) process tool. The manufacturing process system including the multipass cell assembly of the present disclosure may be utilized for production of semiconductor products, flat-panel displays, solar panels, or other products.

In such applications, the multipass cell assembly including an arcuate circumscribing member defining the multipass optical reflection chamber may be employed to improve the signal-to-noise character of the monitoring signal, in relation to a corresponding linear monitoring cell assembly, without appreciable diminution of the overall signal intensity even though the circular geometry provides increased optical surfaces as compared to the linear cell assembly.

Figure 18:
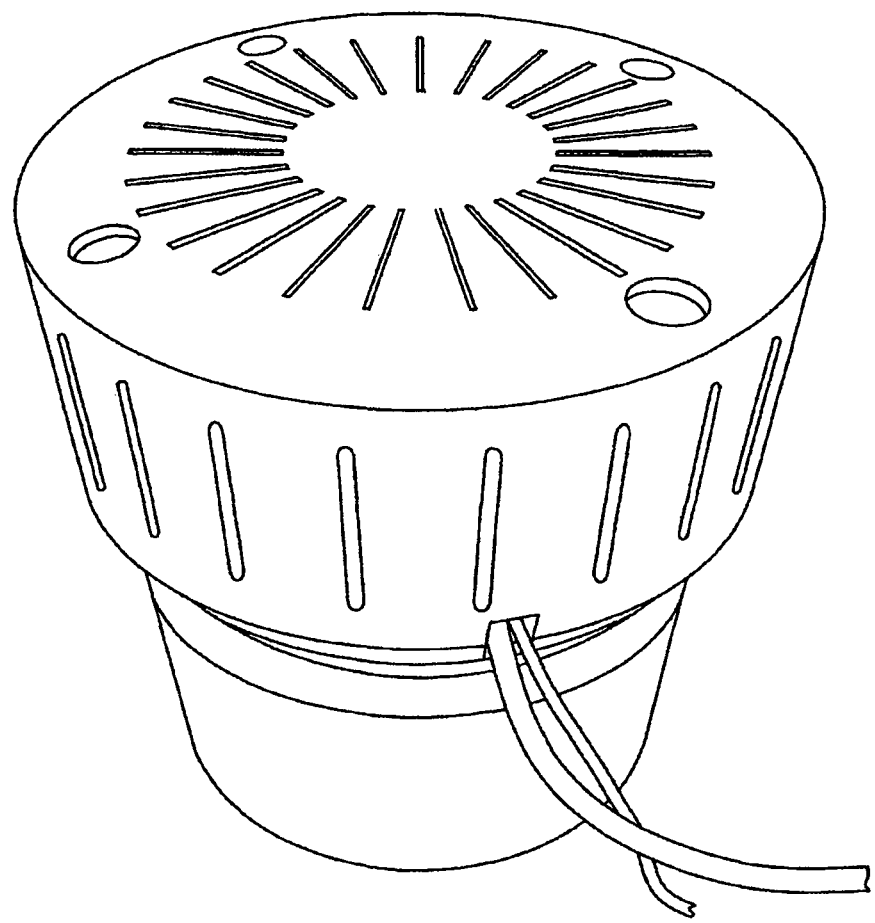
FIG. 18 is a perspective view of a multipass cell assembly according to another embodiment of the present disclosure.

In another embodiment, the multipass cell assembly of the present disclosure may be configured within a housing as shown in FIG. 18, coupled by a power cable to a suitable source of electrical energy, and with a USB cable attached to the cell for transmission of monitoring signal data to an associated processor, which may comprise a microprocessor, programmable logic device, special purpose programmable computer, or the like, as configured to process the monitoring signal data and provide a corresponding output, e.g., as utilized for the purpose of monitoring and control of the gas supply equipment being used to supply the gas being monitored. The gas supply equipment may for example comprise a precursor vapor, which is generated by heating of a corresponding vaporizer vessel containing a solid precursor, so that the solid precursor is volatilized to form corresponding precursor vapor for delivery to the downstream process tool. The multipass cell assembly in such circumstance may be equipped with a heater jacket, to prevent condensation or solidification of the precursor vapor or components thereof, so that the monitoring operation is carried out in an effective manner.

The multipass cell assembly of a type as shown in FIG. 18 may be configured with a suitable beam source, such as an infrared source that is pulsed at an appropriate frequency and otherwise constituted to provide an appropriate signal-to-noise ratio in operation. In a specific embodiment, the pulsing frequency is 10 Hz. The multipass cell assembly is constructed and arranged to reduce thermal drift and minimize extraneous noise, and to provide suitably fast response time, with low thermal drift, a small footprint, and modular design.

Figure 19:
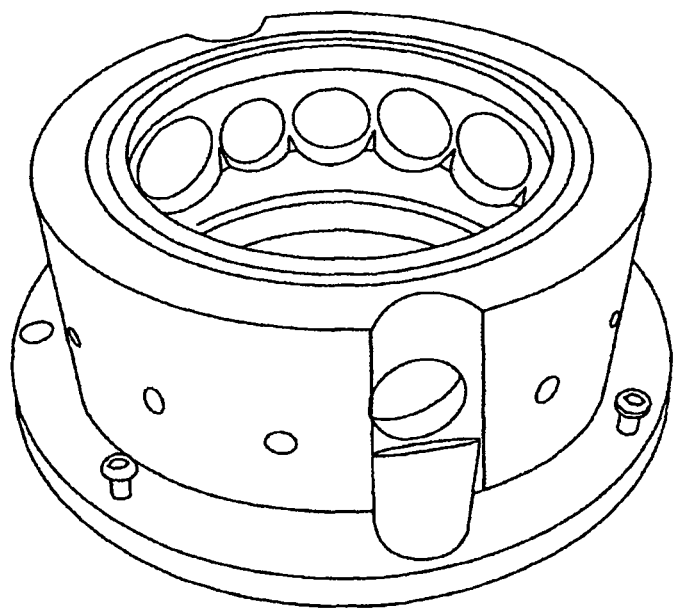
FIGS. 19 and 20 are perspective views of a 3-D printed aluminum composite component of a multipass cell assembly according to one embodiment of the present disclosure, utilizing gold-coated mirrors and configured so that no optical alignment is required after assembly.
Figure 20:
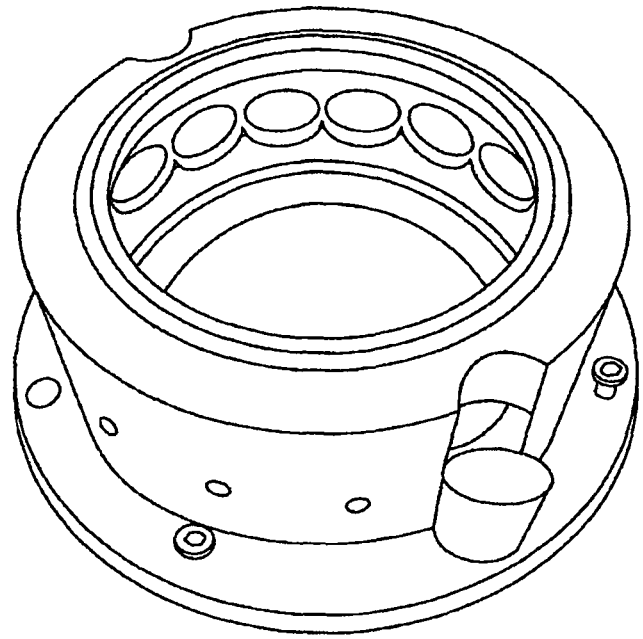

FIGS. 19 and 20 are perspective views of a 3-D printed aluminum composite component of a multipass cell assembly according to one embodiment of the present disclosure, utilizing gold-coated mirrors and configured so that no optical alignment is required after assembly.

Figure 21:
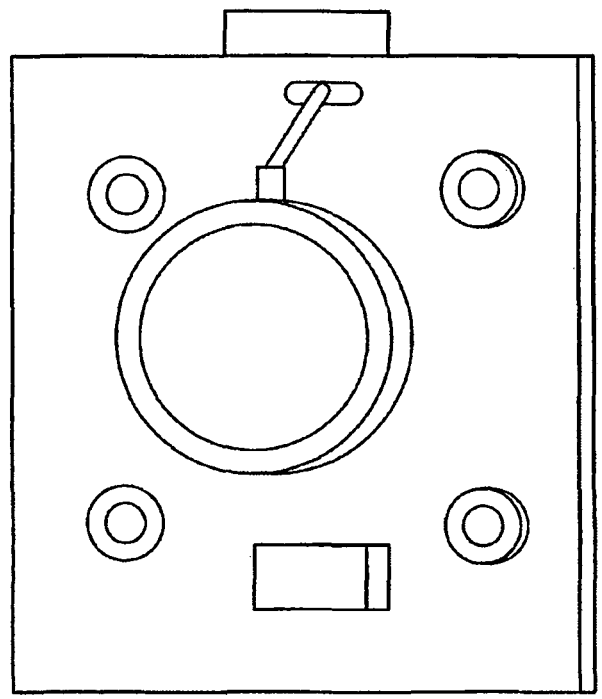
FIG. 21 is an elevation view of an infrared source that may be utilized in the multipass cell assembly of FIGS. 18-20.

FIG. 21 is an elevation view of an infrared source that may be utilized in the multipass cell assembly described in connection with FIGS. 18-20. As indicated, the infrared source may be pulsed at suitable frequency, e.g., 10 Hz, has a compact design, and exhibits low power consumption.

Figure 22:
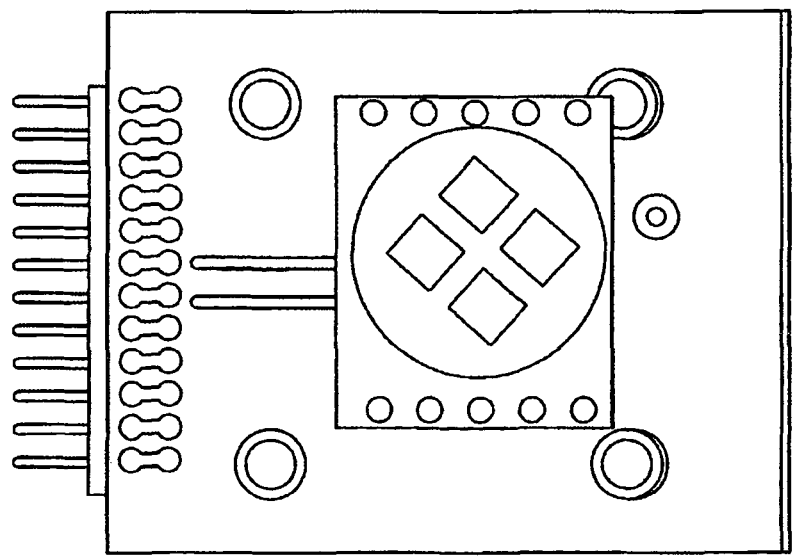
FIG. 22 is an elevation view of a 4 channel detector that may be utilized in the multipass cell assembly of FIGS. 18-20.

FIG. 22 is an elevation view of a 4 channel detector that may be utilized in the multipass cell assembly described in connection with FIGS. 18-20. The detector may be provided in a compact "quad" board configuration, as shown, which is constructed to exhibit suitably low temperature sensitivity and noise sensitivity characteristics.

Figure 23:
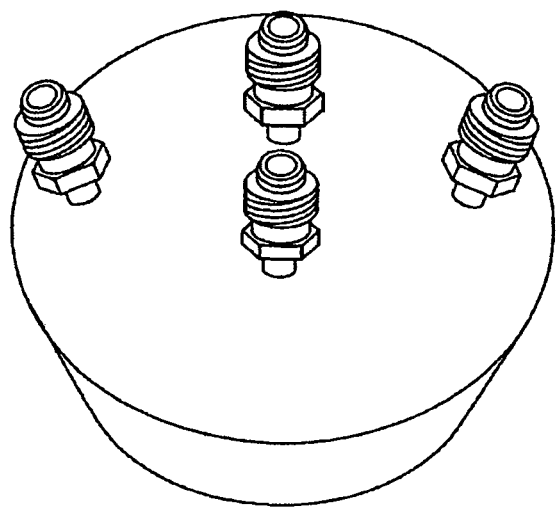
FIG. 23 is a bottom plan view of the multipass cell assembly, in which the gas connections to the unit are shown, as utilized to transmit gas into the cell for the monitoring operation, and to discharge the monitored gas from the cell.
Figure 24:
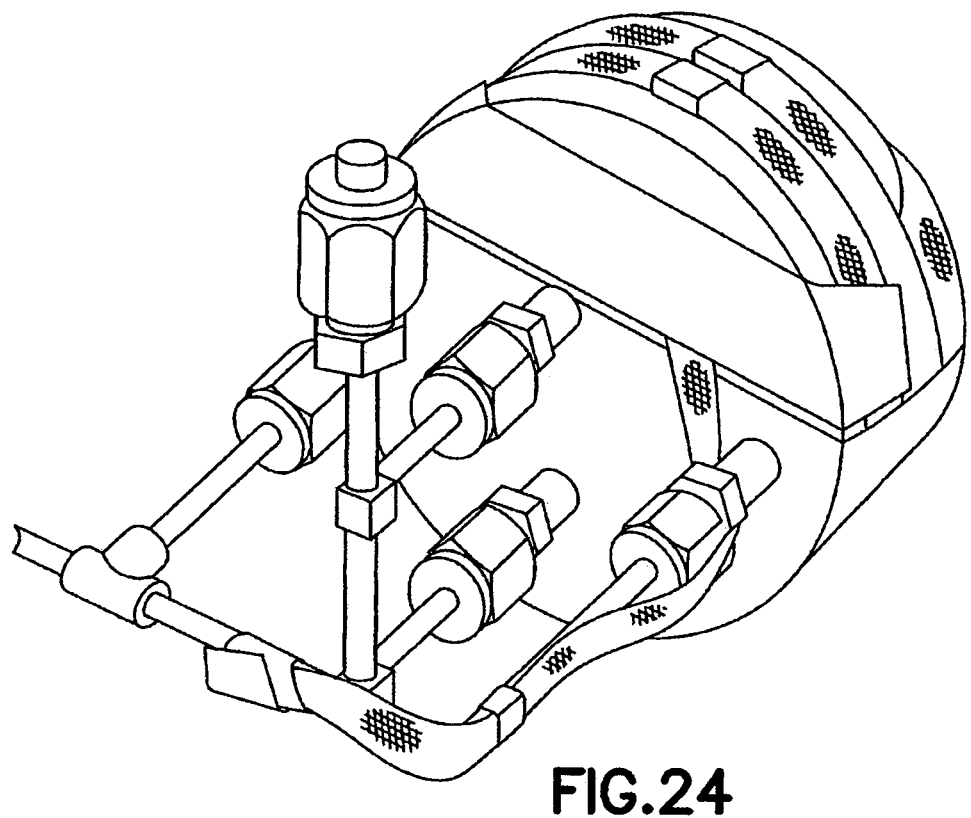
FIG. 24 is a perspective view of such gas connections with attached gas flow lines.

FIG. 23 is a bottom plan view of the multipass cell assembly described above, in which the gas connections to the unit are shown, as utilized to transmit gas into the cell for the monitoring operation, and to discharge the monitored gas from the cell. FIG. 24 is a perspective view of such gas connections with attached gas flow lines.

Figure 25:
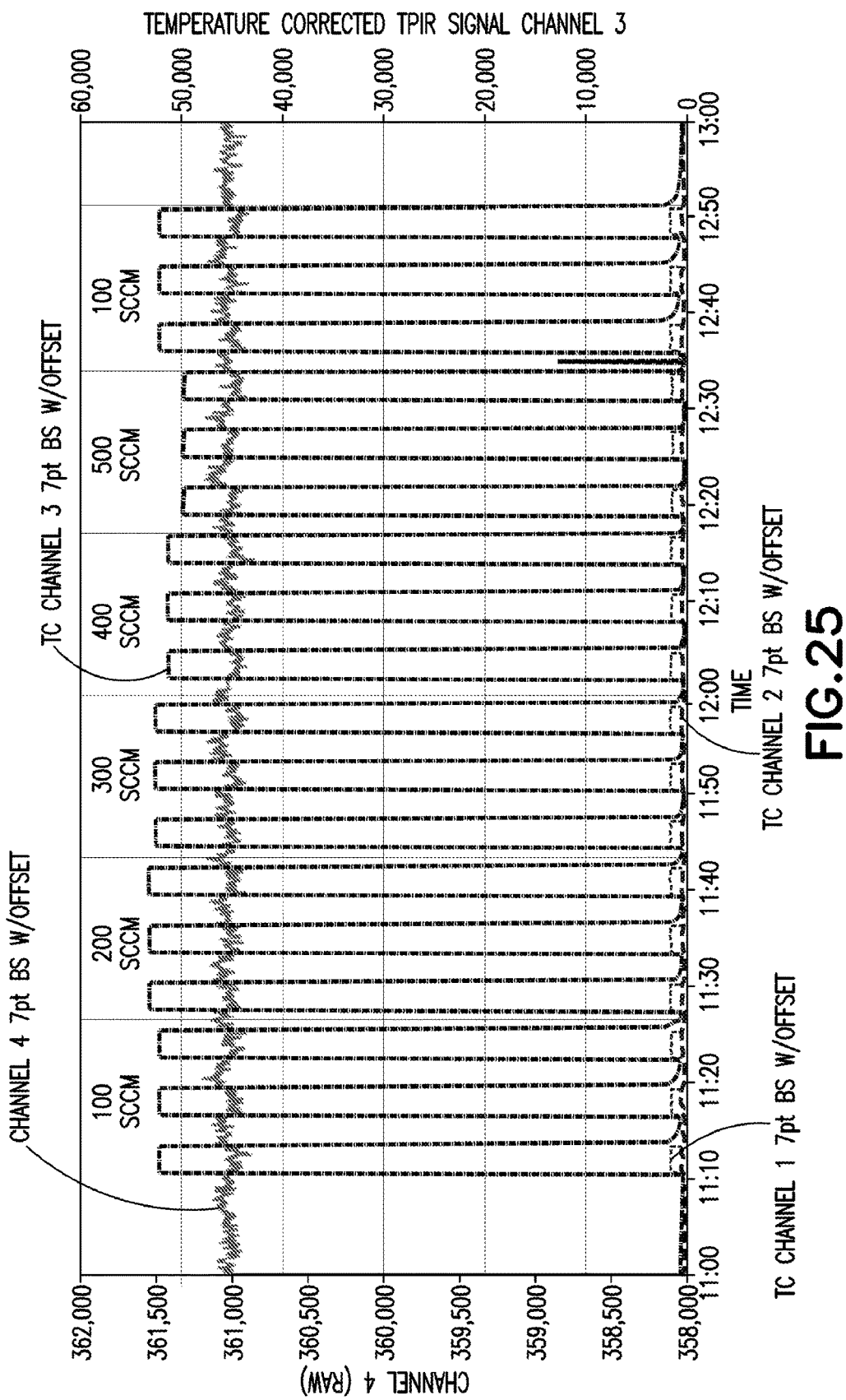
FIG. 25 is a graph of output data as a function of time for a linear cell assembly monitoring a vapor stream including vapor from a vaporizer supplying a tungsten carbonyl precursor vapor, and nitrogen carrier gas, as representative of a vapor stream used for tungsten metallization of a semiconductor substrate in a vapor deposition operation.

FIG. 25 is a graph of output data as a function of time for a linear cell assembly monitoring a vapor stream including vapor from a vaporizer supplying a tungsten carbonyl precursor vapor, and nitrogen carrier gas, as representative of a vapor stream used for tungsten metallization of a semiconductor substrate in a vapor deposition operation.

The monitoring data of FIG. 25 were generated for a gas stream at temperature of 55° C., and pressure of 40 torr, comprising tungsten carbonyl precursor vapor in a combined argon/nitrogen carrier gas stream, at an argon carrier gas flow rate of 500 sccm and a nitrogen carrier gas flow rate of 50 sccm. The consolidated vapor including the carrier gas and the tungsten carbonyl precursor vapor was flowed to the linear cell assembly, and the assembly included a 4-channel infrared detector. The radiation inputted to the linear cell assembly was infrared radiation.

The first channel of the four-channel detector monitored carbon monoxide (CO), indicated by the blue line ———, the second channel monitored carbon dioxide ($CO_2$), indicated by the magenta line ———, the third channel monitored the tungsten carbonyl precursor, indicated by the green line ———, and the fourth channel was a reference channel, indicated by the red line ———.

Figure 26:
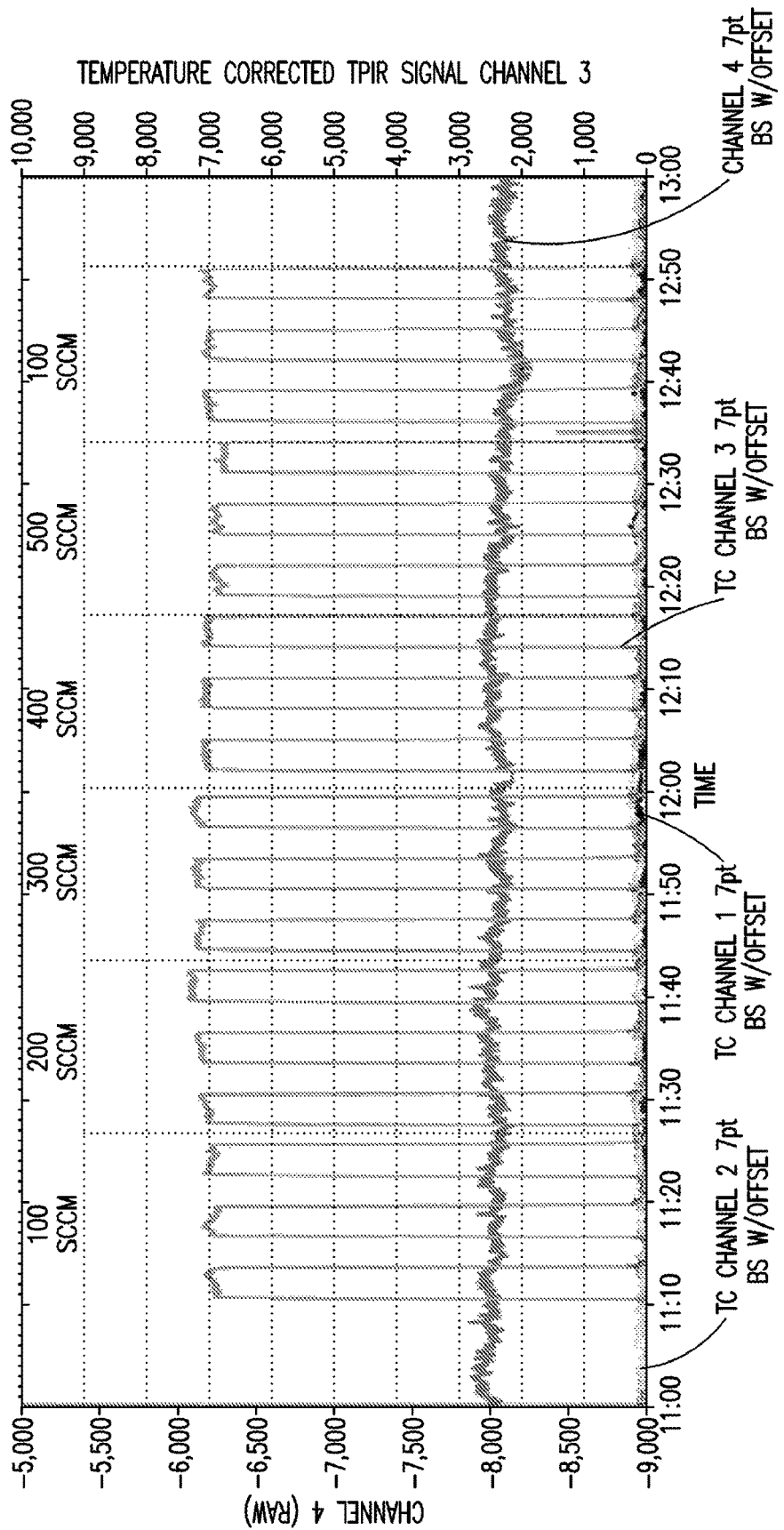
FIG. 26 is a graph of output data as a function of time for a multipass cell assembly of the present disclosure, monitoring a vapor stream including vapor from a vaporizer supplying a tungsten carbonyl precursor, with a nitrogen carrier gas, as representative of a vapor stream used for tungsten metallization of a semiconductor substrate in a vapor deposition operation, under operating conditions corresponding to that used to generate the data in the graph of FIG. 25.

FIG. 26 is a graph of output data as a function of time for a multipass cell assembly of the present disclosure, monitoring a vapor stream including vapor from a vaporizer supplying a tungsten carbonyl precursor, with a nitrogen carrier gas, as representative of a vapor stream used for tungsten metallization of a semiconductor substrate in a vapor deposition operation, under operating conditions corresponding to that used to generate the data in the graph of FIG. 25.

Thus, the monitoring data of FIG. 26 was also generated for a gas stream at temperature of 55° C., and pressure of 40 torr, comprising tungsten carbonyl precursor vapor in a combined argon/nitrogen carrier gas stream, at an argon carrier gas flow rate of 500 sccm and a nitrogen carrier gas flow rate of 50 sccm. The consolidated vapor including the carrier gas and the tungsten carbonyl precursor vapor was flowed to the multipass cell assembly of the present disclosure, and the assembly included a 4-channel infrared detector. The radiation inputted to the multipass cell assembly was infrared radiation.

The first channel of the four-channel detector associated with the multipass cell assembly monitored carbon monoxide (CO), indicated by the blue line ———, the second channel monitored carbon dioxide ($CO_2$), indicated by the magenta line ———, the third channel monitored the tungsten carbonyl precursor, indicated by the green line ———, and the fourth channel was a reference channel, indicated by the red line ———.

A comparison of the data for the linear cell assembly in the FIG. 25 graph and that of the multipass cell assembly of the present disclosure in the FIG. 26 graph indicates that the multipass cell assembly was highly effective in monitoring the composition of the gas stream with respect to CO, $CO_2$, and the tungsten carbonyl compound. No volume hold up or condensation was noted in the multipass cell assembly.

Figure 27:
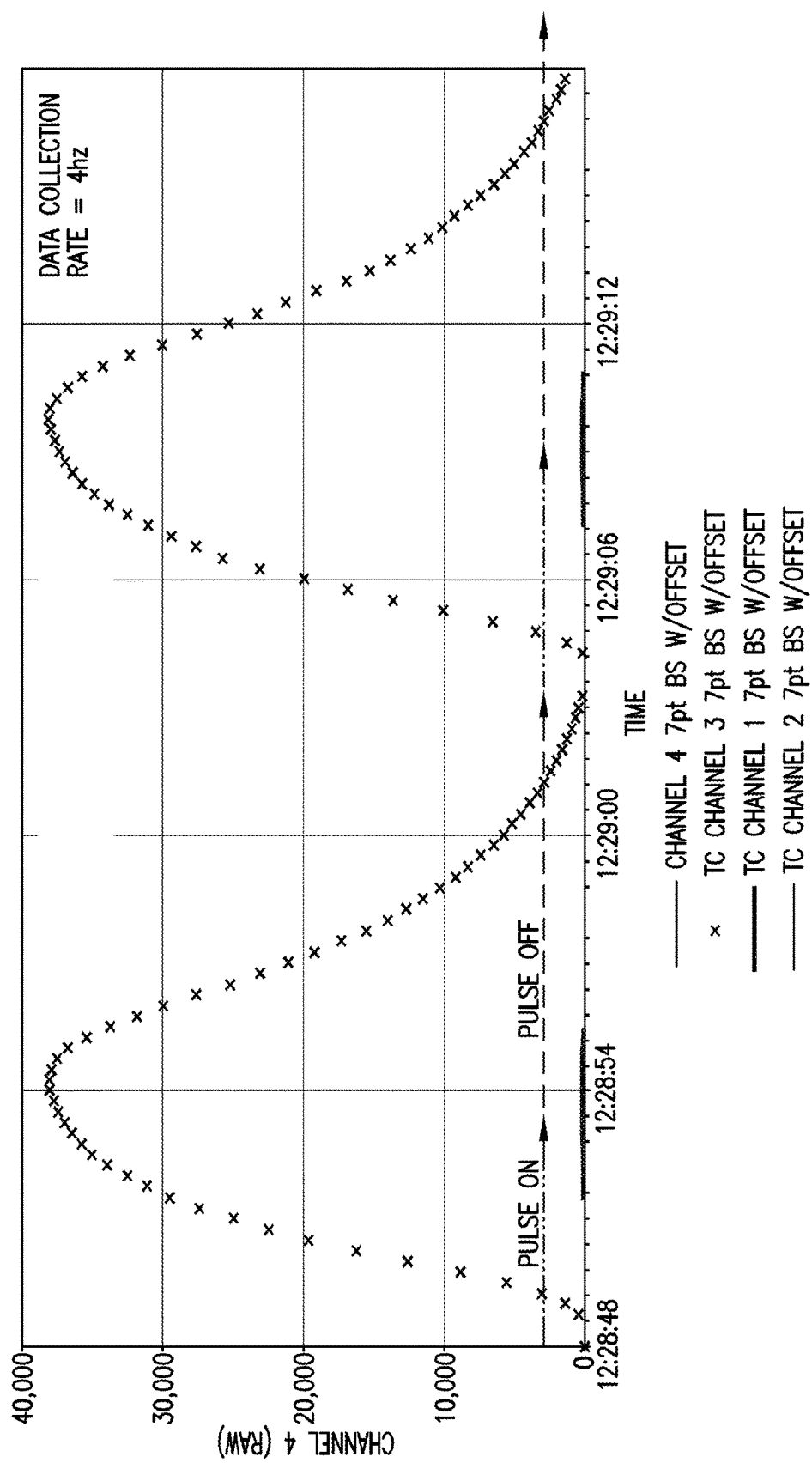
FIG. 27 is a graph of output data (2 pulses) as a function of time for a 1 m linear cell assembly monitoring a gas stream at temperature of 55° C., and pressure of 40 torr, comprising argon at a gas flow rate of 500 sccm.

FIG. 27 is a graph of output data (2 pulses) as a function of time for a 1 m linear cell assembly monitoring a gas stream at temperature of 55° C., and pressure of 40 torr, comprising argon at a gas flow rate of 500 sccm. The monitoring system comprised the linear cell assembly including a 4-channel infrared detector. The radiation inputted to the linear cell assembly was infrared radiation. The pulsed operation included a pulse "ON" of 5 seconds duration, and a 10 seconds "OFF" duration for the 1 m linear cell, with data collection at a rate of 4 Hz.

Figure 28:
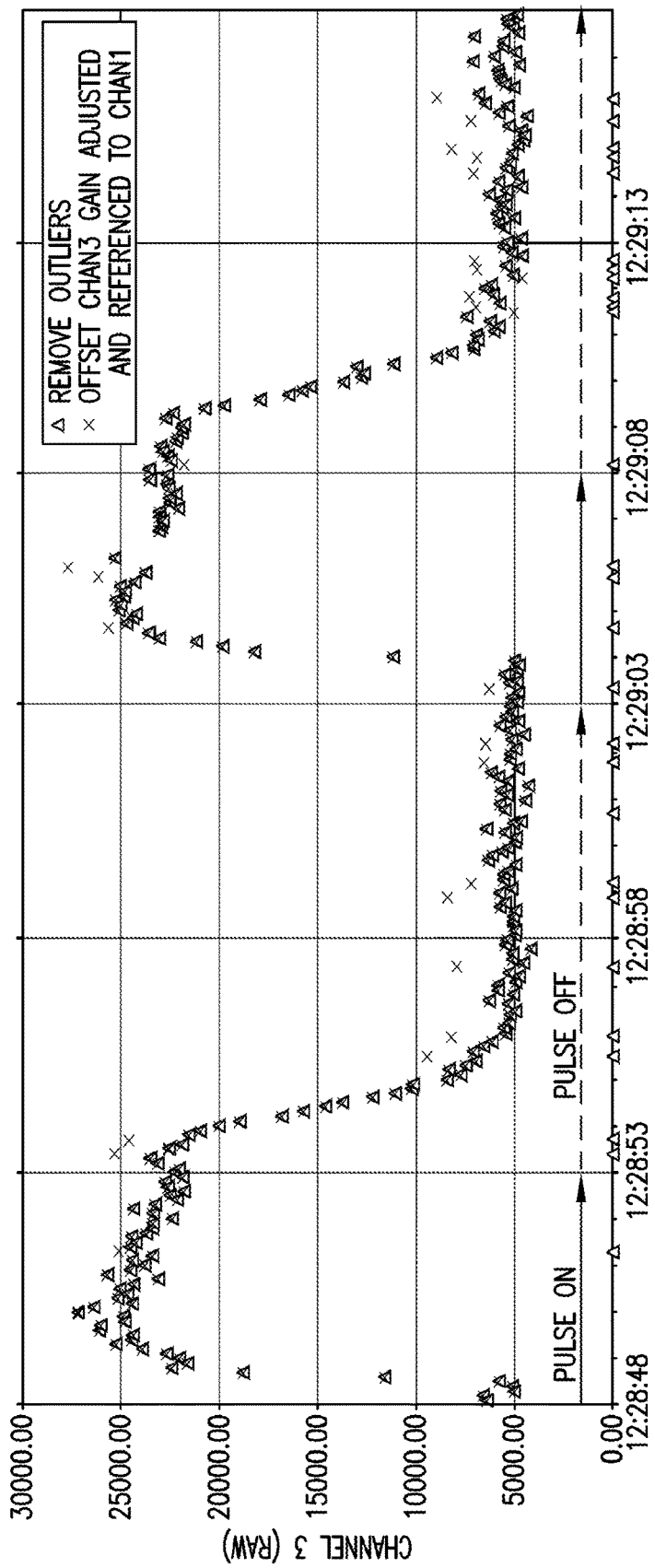
FIG. 28 is a corresponding graph of output data (2 pulses) as a function of time for a multipass cell assembly of the present disclosure, monitoring a gas stream at temperature of 55° C., and pressure of 40 torr, comprising argon carrier gas at a flow rate of 500 sccm.

FIG. 28 is a corresponding graph of output data (2 pulses) as a function of time for a multipass cell assembly of the present disclosure, monitoring a gas stream at temperature of 55° C., and pressure of 40 torr, comprising argon carrier gas at a flow rate of 500 sccm. The monitoring system comprised the multipass cell assembly including a 4-channel infrared detector. The radiation inputted to the multipass cell assembly was infrared radiation. The pulsed operation included a pulse "ON" of 5 seconds duration, and a 10 seconds "OFF" duration for the multipass cell, with data collection at a rate of 10 Hz. A comparison of FIGS. 27 and 28 shows that the multipass cell assembly of the present disclosure provided faster overall response with more information and with the pulse shape being visible, as compared to the linear monitoring cell assembly.

Figure 29:
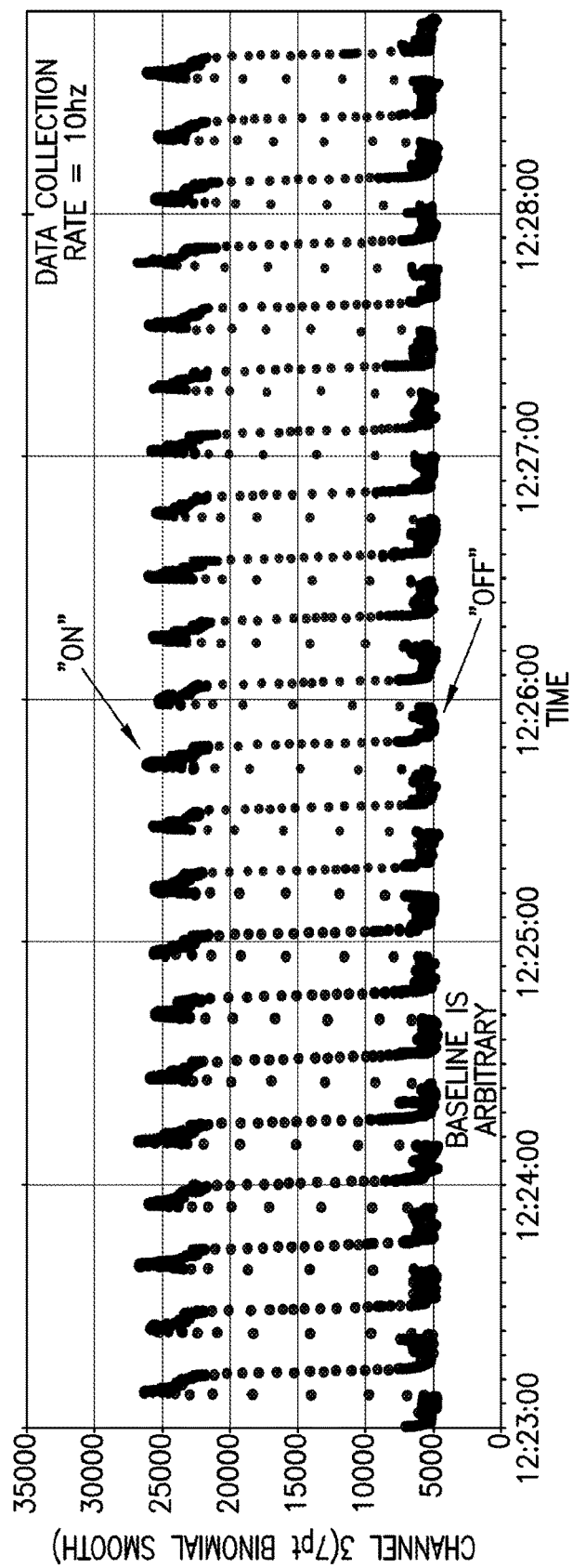
FIG. 29 is a graph of output data (22 pulses) as a function of time for a multipass cell assembly of the present disclosure, monitoring a gas stream at temperature of 55° C., and pressure of 40 torr, comprising argon carrier gas at a flow rate of 500 sccm.

FIG. 29 is a graph of output data (22 pulses) as a function of time for a multipass cell assembly of the present disclosure, monitoring a gas stream at temperature of 55° C., and pressure of 40 torr, comprising argon carrier gas at a flow rate of 500 sccm. The pulsed operation for the multipass cell included a pulse "ON" of 5 seconds duration, and a 10 seconds "OFF" duration, with data collection at a rate of 10 Hz.

Figure 30:
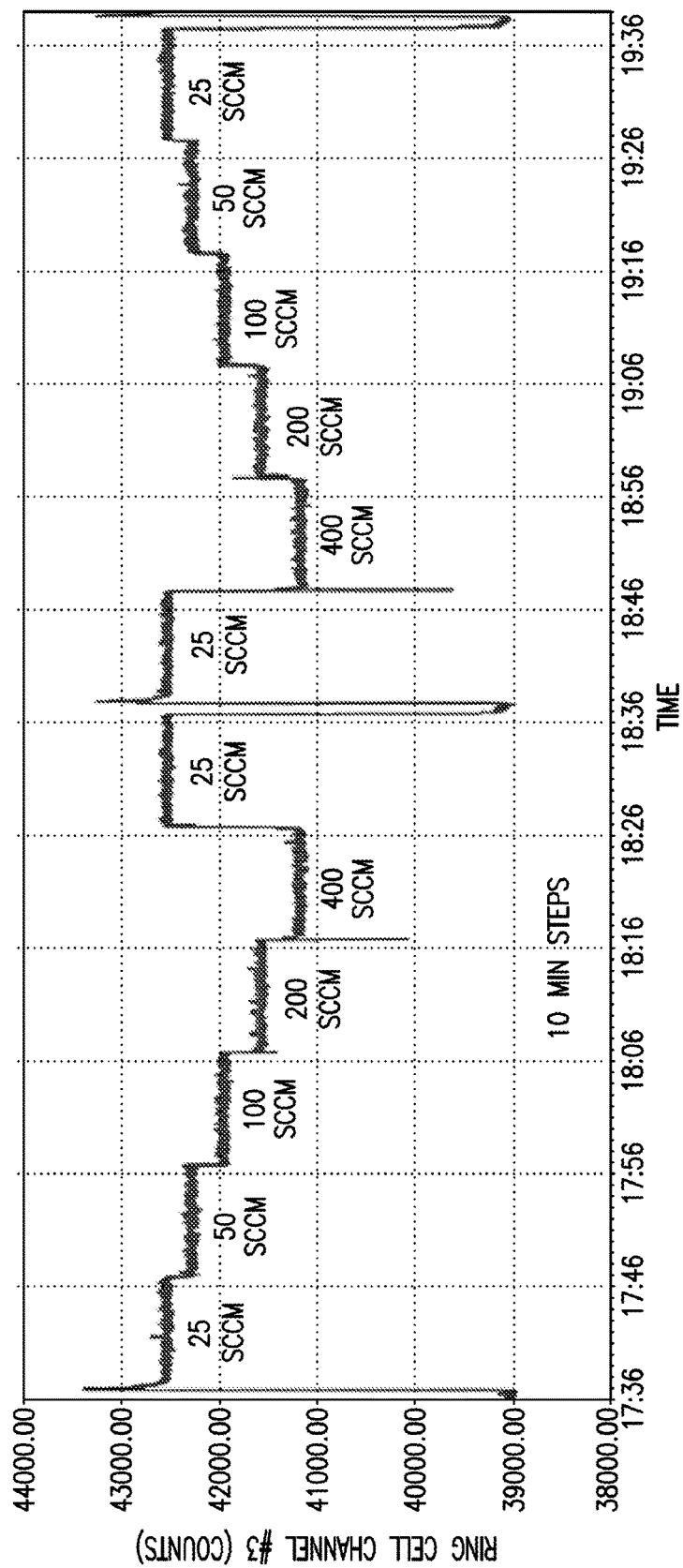
FIG. 30 is a graph of output data for tungsten carbonyl precursor vapor as a function of time, in the form of a concentration staircase measurement for a multipass cell assembly of the present disclosure.

FIG. 30 is a graph of output data for tungsten carbonyl precursor vapor as a function of time, in the form of a concentration staircase measurement for a multipass cell assembly of the present disclosure. The tungsten carbonyl precursor stream was at temperature of 55° C. and at pressure of 40 torr with nitrogen carrier gas flow rate of 50 sccm. The performance of the multipass cell assembly was identical over time, for 6 repeats.

Overall, the multipass cell assembly of the present disclosure exhibited general performance trends in agreement with the linear cell assembly, and demonstrated superiority over the linear cell assembly in terms of improved behavior toward temperature fluctuations, improved behavior towards electronic noise, and faster signal response times, with no hold-up being observed.

While the disclosure has been set forth herein in reference to specific aspects, features and illustrative embodiments, it will be appreciated that the utility of the disclosure is not thus limited, but rather extends to and encompasses numerous other variations, modifications and alternative embodiments, as will suggest themselves to those of ordinary skill in the field of the present disclosure, based on the description herein. Correspondingly, the disclosure as hereinafter claimed is intended to be broadly construed and interpreted, as including all such variations, modifications and alternative embodiments, within its spirit and scope.

What is claimed is:

1. A multipass cell assembly for monitoring of fluid, comprising:
    a multipass optical reflection chamber comprising a cylindrical wall, the cylindrical wall comprising circumferentially spaced-apart openings therein;
    mirrors disposed within the circumferentially spaced-apart openings, the mirrors being inwardly facing;
    a light input structure comprising a light source, wherein light from the light source is directed onto a reflective surface of one or more of the mirrors so that multipass optical reflection of light is generated in the optical reflection chamber;
    a light output structure through which multipassed light is directed out of the optical reflection chamber for detection and processing thereof;
    a fluid inlet through which fluid is introduced into the multipass optical reflection chamber so that it interacts with multipassing light therein; and
    a fluid outlet through which fluid is discharged from the multipass optical reflection chamber after interaction with multipassing light therein.

2. The multipass cell assembly of claim 1, further comprising cover and floor members that cooperatively engage with the cylindrical wall to enclose the multipass optical reflection chamber.

3. The multipass cell assembly of claim 1, wherein the light input structure comprises a light input port, and wherein the light output structure comprises a light output port.

4. The multipass cell assembly of claim 3, wherein the light input port and the light output port define an included angle therebetween in a range of from 30° to 90°.

5. The multipass cell assembly of claim 3, wherein the light input port and the light output port define an included angle therebetween in a range of from 35° to 75°.

6. The multipass cell assembly of claim 1, wherein the cylindrical wall comprises aluminum composite material.

7. The multipass cell assembly of claim 1, further comprising cover and floor members cooperatively engaging the cylindrical wall to enclose the multipass optical reflection chamber, and wherein the light source is mounted on the cover member and optically coupled to the light input structure and a light detector is mounted on the cover member and optically coupled to the light output structure.

8. The multipass cell assembly of claim 1, wherein the multipass optical reflection chamber is configured to provide a light path length in a range of from 0.5 to 10 meters.

9. The multipass cell assembly of claim 1, wherein the multipass optical reflection chamber is configured to provide a light path length in a range of from 0.5 to 5 meters.

10. A fluid processing system, comprising
a process tool having a fluid stream; and
the multipass cell assembly of claim 1, wherein the fluid stream flows through the multipass optical reflection chamber from the fluid inlet to the fluid outlet for interaction with multipassing light in the multipass optical reflection chamber.

11. The fluid processing system of claim 10, wherein the process tool comprises a vapor deposition tool.

12. The fluid processing system of claim 11, wherein the vapor deposition tool is configured to deposit tungsten on a semiconductor substrate from a tungsten precursor, and to generate the fluid stream comprising unreacted tungsten precursor.

13. The fluid processing system of claim 11, wherein the vapor deposition tool is configured to deposit tungsten on a semiconductor substrate from a tungsten precursor, and to generate the fluid stream comprising unreacted tungsten precursor and vapor deposition byproducts of the tungsten precursor.

14. A multipass cell assembly for monitoring of fluid, comprising:
a multipass optical reflection chamber comprising a cylindrical wall member, the cylindrical wall member comprising circumferentially spaced-apart openings therein;
mirrors in the circumferentially spaced apart openings, the mirrors being inwardly facing;
floor and cover members cooperatively engaged with the cylindrical wall member to enclose the multipass optical reflection chamber;
a light input structure optically coupled to a light source mounted on the cover member, wherein light from the light source is directed onto a reflective surface of one or more of the mirrors so that multipass optical reflection of light is generated in the optical reflection chamber;
a light output structure optically coupled to a light detector mounted on the cover member and through which multipassed light is directed out of the optical reflection chamber for detection and processing thereof;
a fluid inlet comprising at least one fluid inlet port in the floor member through which fluid is introduced into the multipass optical reflection chamber so that it interacts with multipassing light therein; and
a fluid outlet comprising at least one fluid outlet port in the floor member through which fluid is discharged from the multipass optical reflection chamber after interaction with multipassing light therein.

15. A method of monitoring a fluid stream, comprising:
flowing the fluid stream through a multipass cell assembly for monitoring fluid, wherein the multipass cell assembly comprises:
a multipass optical reflection chamber comprising a cylindrical wall, the cylindrical wall comprising circumferentially spaced-apart openings therein;
mirrors disposed within the circumferentially spaced-apart openings, the mirrors being inwardly facing;
a light input structure comprising a light source, wherein light from the light source is directed onto a reflective surface of one or more of the mirrors so that multipass optical reflection of light is generated in the optical reflection chamber;
a light output structure through which multipassed light is directed out of the optical reflection chamber for detection and processing thereof;
a fluid inlet through which fluid is introduced into the multipass optical reflection chamber so that it interacts with multipassing light therein; and
a fluid outlet through which fluid is discharged from the multipass optical reflection chamber after interaction with multipassing light therein;
generating a multipassed light output; and
detecting and processing the multipassed light output to characterize or analyze the fluid stream.

* * * * *